(12) United States Patent
Boyle

(10) Patent No.: US 6,346,633 B1
(45) Date of Patent: Feb. 12, 2002

(54) ANTI-TUMUOR AGENTS

(75) Inventor: Francis T Boyle, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/646,459

(22) PCT Filed: Mar. 16, 1999

(86) PCT No.: PCT/GB99/00787

§ 371 Date: Nov. 3, 2000

§ 102(e) Date: Nov. 3, 2000

(87) PCT Pub. No.: WO99/48857

PCT Pub. Date: Sep. 30, 1999

(30) Foreign Application Priority Data

Mar. 20, 1998 (GB) .............................. 9805866

(51) Int. Cl.$^7$ ................... C07C 50/04; C07C 50/06; C07C 9/00; A01N 37/00; A61K 31/215
(52) U.S. Cl. ................ 552/303; 552/293; 514/529
(58) Field of Search ................. 552/303, 293; 514/529

(56) References Cited

FOREIGN PATENT DOCUMENTS

| EP | 0 002 677 | 7/1979 |
| EP | 092 136 | 10/1983 |
| WO | WO 93 11099 | 6/1993 |
| WO | WO 99/48860 | 9/1999 |

OTHER PUBLICATIONS

Wynn et al: "Synthesis and bioevaluation of a series of fatty acid esters of p–(n,n–Bis(2–chloroethyl)amino)phenol" Journal of Pharmaceutical Sciences, vol. 71, No. 7, Jul. 1982, pp. 772–776, XP002105522.

Sykes et al: "Kinetics and mechanism of the cyclization of substituted n–phenyl–2–methyl–2–(2–aminophenyl) propana mides and analogues" Journal of the Chemical Society, Perkins Transactions 2, 1995, pp. 337–342, XP002105523.

Carpino et al: "Reductive Tactonization of strategically methylated quinnone propionic acid esters and amides", Journal of Organic Chemistry, vol. 54, No. 14, Jul. 7, 1989, pp. 3303–3310, XP002105524.

Chikhale et al: "Tumor targeted Prodrugs: Redox–Activation of Conformationally Constrained, Bioreductive Melphalan Prodrugs", Proceedings of the 88$^{th}$, Annual Meeting of the American Association for Cancer Research, Apr. 12–16, 1997, vol. 38, Apr. 12, 1997, p. 432, XP002052354.

Atwell et al., "Relationships between Structure and Kinetics of Cyclization of 2–Aminoaryl Amides: Potential Prodrugs of Cyclization–Activated Aromatic Mustards", J. Med. Chem. 1994, vol. 37, pp. 371–380.

Ross et al., "Arly–2–halogenoalkylamines. Part XIV. * Some Compounds posessing latent Cytotojxic Activity;" Journal of the Chemical Society, 1995, pp. 3110–3116, XP002105519.

Sasiela et al., "Bioreductively–activated antitumor drug delivery systems designed to optimize solid tumor targeting and avoid neurotoxicity." Pharmacology and Experimental Therapeutics, Proceedings of the American Association for Cancer Rsearch, Mar. 1998, vol. 39, pp. 426.

*Primary Examiner*—Paul J. Killos
*Assistant Examiner*—Mahreen Chaudhry
(74) *Attorney, Agent, or Firm*—Pillsbury Winthrop LLP

(57) ABSTRACT

The invention concerns anti-tumour agents of formula (I) wherein each of $R^1$, $R^2$ and $R^3$ has the meanings defined in the specification including hydrogen, (1–4C)alkyl, (3–4) alkenyl, (3–4C)alkynyl, amino, (1–4C)alkylamino and (1–4C)alkoxy; each of $R^4$ and $R^5$ is (1–4C)alkyl; each of $R^6$ and $R^7$ is hydrogen or (1–4C)alkyl; X is oxygen; m is 1 or 2 and each $R^8$ is as defined in the specification; each of $Y^1$ and $Y^2$ is halogeno, (1–4C)alkanesulphonyloxy, benzene-sulphonyloxy or phenyl-(1–4C)akanesulphonyloxy; or a pharmaceutically-acceptable salt thereof; provided that at least one of $R^1$, $R^2$ and $R^3$ is other than hydrogen; a process for preparation, pharmaceutical compositions containing them and their use in the production of an anti-proliferative effect.

(I)

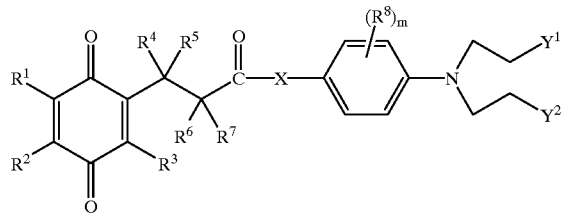

11 Claims, No Drawings

ANTI-TUMUOR AGENTS

This application is the nation phase of international application PCT/GB99/00787 filed Mar. 16, 1999 which designated the U.S.

The invention relates to cytotoxic anti-tumour agents. More particularly the invention relates to novel (1,4-benzoquinonyl)alkanoic acid derivatives which bear a substituent comprising a cytotoxic nitrogen mustard moiety. The invention also relates to processes for the preparation of said (1,4-benzoquinonyl)alkanoic acid derivatives, to pharmaceutical compositions containing them and to their use in the production of an anti-tumour effect in a warm-blooded animal such as man.

Many of the current treatments for cell proliferation diseases such as cancer and psoriasis utilise cytotoxic agents which inhibit DNA synthesis or cell division. Such compounds tend to lack specificity and can be toxic to cells generally as neoplastic cells are usually only slightly different from normal cells. The toxic effect of the cytotoxic agent on rapidly dividing tumour cells can be beneficial but normal cells in which continual cell division occurs such as bone marrow cells and gut epithelial cells can also be adversely affected.

There are particular difficulties in obtaining an effective treatment of solid tumours using either chemotherapy with cytotoxic agents or radiotherapy as, within the inner hypoxic regions of the tumour mass where the network of blood capillaries is deficient, cell division is slow or absent. Such hypoxic regions exist in most major classes of solid tumours, for example in bladder, breast, cervical, colorectal, head and neck, lung, ovarian, pancreatic, prostate and stomach tumours. In particular it has been shown by analysis of clinical samples that a significant proportion of most head and neck, breast and cervical tumours, for example between 10% and 30% of the tumour mass, is severely hypoxic with an oxygen tension below 5 mm Hg (0.0066 bar).

It has been recognised that the presence of such hypoxic regions within solid tumours could present an opportunity to allow a more selective cytotoxic drug therapy based on either a prodrug or double-prodrug approach. For example, a prodrug approach is disclosed by B. D. Palmer et al., *J. Med. Chem.* 1992, 35, 3214–3222, and in International Patent Application WO 93/11099 concerning a nitro-substituted anilino-mustard compound which may be capable of reduction to a more potent amino-substituted anilino-mustard. A problem with this approach was that those additional substituents which were necessary to allow rapid enzymatic reduction of the nitro group tended to diminish the cytotoxic potency of the resultant amino-substituted compound. The double-prodrug approach was taken up to address this problem. For example, it is disclosed by G. J. Atwell et al., *J. Med. Chem.*, 1994, 37, 371–380, and B. M. Sykes et al., *J. Chem. Soc. Perkin Transact. II*, 1995, 337–342, that certain N-{4-[bis(2chloroethyl)amino] phenyl}-2-nitrophenylacetamide derivatives could be reduced to the corresponding 2-aminophenylacetamide derivatives which could cyclise to release the anilino mustard 4-[bis(2-chloroethyl)amino]aniline. An alternative double-prodrug approach involves the interconversion in biological systems of quinone and hydroquinone moieties. For example, it is disclosed by L. A. Carpino et al., *J. Org. Chem.*, 1989, 54, 3303–3310, that certain (1,4-benzoquinonyl)alkanoic acid derivatives could provide a feasible approach for the delivery of a cytotoxic agent. Model compounds which were prepared included N,N-di-(2-chloroethyl)-3-(2-methoxy-3,5-dimethyl-1,4-benzoquinonyl)-3-methylbutyramide and N,N-di-(2-chloroethyl)-3-(2,3-dimethoxy-5-methyl-1,4-benzoquinonyl)-3-methylbutyramide which were designed to release the simple mustard bis(2-chloroethyl)amine. It is further known from *Proceedings of the American Association for Cancer Research*, 1997, 38, 433–434 (Abstract No. 2894) that the cytotoxic mustard drug melphalan can be linked to a (1,4-benzoquinonyl)alkanoic acid. It was noted that the fastest in vitro bio-reductive activation of certain prodrugs was of the order of 25% per hour i.e. a $t_{1/2}$ of approximately 2.5 hours and this was linked to reduction potentials in the range –480 to –520 mV. In contrast a slower in vitro bio-reductive activation of other prodrugs of the order of 10% per hour i.e. a $t_{1/2}$ of approximately 6 hours was linked to a reduction potential of the order of –730 mV.

It is an object of the present invention to provide double-prodrug quinone compounds which on reduction to the hydroquinone rapidly break down to release the cytotoxic agent.

The present invention provides an anti-tumour agent of the formula I

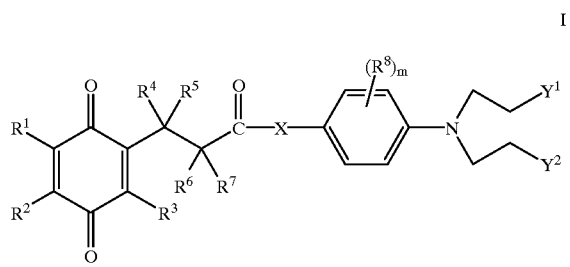

wherein $R^1$ is hydrogen, (1–4C)alkyl, (1–4C)alkenyl, (1–4C)alkynyl, hydroxy-(1–4C)alkyl, (1–4C)alkoxy-(1–4C) alkyl, amino-(1–4C)alkyl, (1–4C)alkylamino-(1–4C)alkyl, di-[(1–4C)alkyl]amino-(1–4C)alkyl, pyrrolidin-1-yl(1–4C) alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, carboxy-(1–4C)alkyl, (1–4C)alkoxycarbonyl-(1–4C)alkyl, carbamoyl-(1–4C)alkyl, N-(1–4C) alkylcarbamoyl-(1–4C)alkyl, N,N-di-[(1–4C)alkyl] carbanoyl-(1–4C)galkyl, amino, (1–4C)alkylamino, (3–4C) alkenylamino, (3–4C)alkynylamino, di-[(1–4C)alkyl] amino, di-[(3–4C)alkenyl]amino, di-[(3–4C)alklenyl] amino, pyrrolidin-1-yl, piperidino, morpholino, piperazin-1-yl, 4-(1–4C)alkylpiperazin-1-yl, hydroxy-(2–4C) alkylamino, (1–4C)alkoxy-(2–4C)alkylamino, amino-(2–4C)alkylamino, (1–4C)alkylamino-(2–4C)alkylamino, di-[(1–4C)alkyllamino-(2–4C)alkylamino, pyrrolidin-1-yl-(2–4C)alkylamino, piperidino-(2–4C)alkylamino, morpholino-(2–4C)alkylamino, piperazin-1-yl-(2–4C) alkylamino, 4-(1–4C)alkylpiperazin-1-yl-(2–4C) alkylamino, (2–4C)alkanoylamino, (2–4C)alkanoylamino-(2–4C)alkylamino, carboxy-(1–4C)alkylamino, (1–4C) alkoxycarbonyl-(1–4C)alkylamino, carbamoyl-(1–4C) alkylamino, N-(1–4C)alkylcarbamoyl-(1–4C)alkylamino, N,N-di-[(1–4C)alkyl]carbamoyl-(1–4C)alkylamino, hydroxy, (1–4C)alkoxy, hydroxy-(2–4C)alkoxy, (1–4C) alkoxy-(2–4C)alkoxy, amino-(2–4C)alkoxy, (1–4C) alkylamino-(2–4C)alkoxy, di-[(1–4C)alkyl]amino-(2–4C) alkoxy, pyrrolidin-1-yl-(2–4C)alkoxy, piperidino-(2–4C) alkoxy, morpholino-(2–4C)alkoxy, piperazin-1-yl-(2–4C) alkoxy or 4-(1–4C)alkylpiperazin-1-yl-(2–4C)alkoxy;

$R^2$ is hydrogen, (1–4C)alkyl, (3–4C)alkenyl, (3–4C) alkynyl, hydroxy-(1–4C)alkyl, (1–4C)alkoxy-(1–4C) alkyl, amino-(1–4C)alkyl, (1–4C)alkylamino-(1–4C)

alkyl, di-[(1–4C)alkyl]amino-(1–4C)alkyl, pyrrolidin-1-yl]-(1–4C)alkyl, piperidino-(1–4C)alkyl, morpholino-(1–4C)alkyl, piperazin-1-yl-(1–4C)alkyl, 4-(2–4C)alkylpiperazin-1-yl-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C) alkyl, amino, (1–4C)alkylamino, (3–4C)alkenylamino, (3–4C)alkynylamino, di-[(1–4C)alkyl]amino, di-[(1–4C)alkenyl]amino, di-[(3–4C)alkynyl]amino, pyrrolidin-1-yl, piperidino, morpholino, piperazin-1-yl, 4-(1–4C)alkylpiperazin-1-yl, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, (2–4C)alkanoylamino, (2–4C)alkanoylamino-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbainoyl-(1–4C)alkylamino, N,N-di-[(1–4C)alkyl]carbamoyl-(1–4C)alkylamino, hydroxy, (1–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy or 4-(1–4C)alkylpiperazin-1-yl-(2–4C)alkoxy;

$R^3$ is hydrogen, (1–4C)alkyl, (1–4C)alkenyl, (3–4C)alkynyl, hydroxy-(1–4C)alkyl, (1–4C)alkoxy-(1–4C)alkyl, amino-(1–4C)alkyl, (1–4C)alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino, (1–4C)alkylamino, (3–4C)alkenylamino, (3–4C)alkynylamino, di-[(1–4C)alkyl]amino, di-[(3–4C)alkenyl]amino, di-[(3–4C)alkynyl]amino, pyrrolidin-1-yl, piperidino, morpholino, piperazin-1-yl, 4-(1–4C)alkylpiperazin-1-yl, hydroxy-(2–4C)alkylamino, (1–4C)alkoxy-(2–4C)alkylamino, amino-(2–4C)alkylamino, (1–4C)alkyamino-(2–4C)alkylamino, di-[(1–4C)alkylgamino-(2–4C)alkylainino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, (2–4C)alkanoylamino, (2–4C)alkanoylamino-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbamoyl-(1–4C)alkylamino, N,N-di-[(1–4C)alkyl]carbamoyl-(1–4C)alkylamino, hydroxy, (1–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino2–4C)alkoxy, morpholino- (2–4C)alkoxy, piperazin-1-yl-(2–4C)alkoxy or 4-(1–4C)alkylpiperazin-1-yl-(2–4C)alkoxy;

$R^4$ is (1–4C)alkyl;
$R^5$ is (1–4C)alkyl;
$R^6$ is hydrogen or (1–4C)alkyl;
$R^1$ is hydrogen or (1–4C)alkyl;
X is oxygen;
m is 1 or 2 and each $R^8$ is independently hydrogen, halogeno, hydroxy, (1–4C)alkoxy, (2–4C)alkenyloxy, (2–4C)alkynyloxy, (1–4C)alkyl, (3–4C)alkenyl, (3–4C)alkynyl, amino, (1–4C)alkylamino, di-[(1–4C)alkyl]amino, cyano, (2–4C)alkanoylamino, carboxy, (1–4C)alkoxycarbonyl, carbamoyl, N-(1–4C)alkylcarbamoyl or
N,N-di-[(1–4C)alkyl]carbamoyl; $Y^1$ is halogeno, (1–4C)alkanesulphonyloxy, benzenesulphonyloxy or phenyl-(1–4C)alkanesulphonyloxy; and $Y^2$ is halogeno, (1–4C)alkanesulphonyloxy, benzenesulphonyloxy or phenyl-(1–4C)alkanesulphonyloxy;

and wherein any heterocyclic group in $R^1$, $R^2$ or $R^3$ is optionally substituted with 1, 2 or 3 (1–4C)alkyl substituents, and wherein any phenyl group in $Y^1$ or $Y^2$ when $Y^1$ and $Y^2$ is benzenesulphonyloxy or phenyl-(1–4C)alkanesulphonyloxy is optionally substituted with 1, 2 or 3 substituents selected from halogeno, nitro, cyano, trifluoromethyl, hydroxy, amino, (1–4C)alkyl, (1–4C)alkoxy, (1–4C)alkylamino and di-[(1–4C)alkyl]amino;

or a pharmaceutically-acceptable salt thereof; provided that at least one of $R^1$, $R^2$ and $R^3$ is other than hydrogen.

Within the present invention it will be observed that an anti-tumour agent of the invention may possess one or more asymmetric carbon atoms and it can therefore exist in diastereoisomeric, racemic and optically active forms. It is to be understood that the invention encompasses any such form which possesses anti-tumour activity, it being a matter of common general knowledge how various diastereoisomeric forms may be separated and how a racemic compound may be separated into its optically-active forms.

It is also to be understood that the compounds of the invention can exist in solvated as well as unsolvated forms such as, for example, hydrated forms. It is to be understood that the invention encompasses all such solvated forms which possess anti-tumour activity.

Suitable values for the generic groups mentioned above are set out below. The term 'alkyl' includes both straight- and branched-chain alkyl groups but references to individual alkyl groups such as 'propyl' are specific for the straight chain version only. An analogous convention applies to other generic terms.

A suitable value for each of $R^1$, $R^2$, $R^3$, $R^4$, $R^5$, $R^6$, $R^7$ and $R^8$ when it is (1–4C)alkyl or for a (1–4C)alkyl substituent on a phenyl or heterocyclic group is, for example, methyl, ethyl, propyl, isopropyl, butyl or isobutyl.

A suitable value for each of $R^1$, $R^2$, $R^3$ and $R^1$ when it is (1–4C)alkoxy or for a (1–4C)alkoxy substituent on a phenyl group is, for example, methoxy, ethoxy, propoxy, butoxy or isobutoxy.

A suitable value for each of $R^1$, $R^2$, $R^3$ and $R^8$ when it is (1–4C)alkylamino or for a (1–4C)alkylamino substituent on a phenyl group is, for example, methylamino, ethylamino, propylamino, isopropylamino, butylamino or isobutylamino.

A suitable value for each of $R^1$, $R^2$, $R^3$ and $R^8$ when it is di-[(1–4C)]alkyl]amino or for a di-[(1–4C)alkyl]amino substituent on a phenyl group is, for example, dimethylamino, diethylamino, N-ethyl-N-methylamino, dipropylamino or di-isopropylamino.

Suitable values for each $R^1$, $R^1$ or $R^3$ group include, for example:

for (3–4C)alkenyl: allyl, methylallyl, 2-butenyl and 3-butenyl;

for (1–4C)alkynyl: 2-propynyl and 2-butynyl;

for hydroxy-(1–4C)alkyl: hydroxymethyl, 1-hydroxyethyl, 2-hydroxyethyl and 3-hydroxypropyl;

for (1–4C)alkoxy-(1–4C)alkyl: methoxymethyl, ethoxymethyl, 1-methoxyethyl, 2-methoxyethyl, 2-ethoxyethyl and 3-methoxypropyl;

for amino-(1–4C)alkyl: aminomethyl, 1-aminoethyl, 2-aminoethyl and 3-aminopropyl;

for (1–4C)alkylamino-(1–4C)alkyl: methylaminomethyl, ethylaminomethyl, 1-methylaminoethyl, 2-methylaminoethyl, 2-ethylamimoethyl and 3-methylaminopropyl;

for di-[(1–4C)alkyl]amino-(1–4C)alkyl: dimethylaminomethyl, diethylaminomethyl, 1-dimethylaminoethyl, 2-dimethylaminoethyl and 3-dimethylaminopropyl;

for pyrrolidin-1-yl-(1–4C)alkyl: pyrrolidin-1-ylmethyl and 2-(pyrrolidin-1-yl)ethyl;

for piperidino-(1–4C)alkyl: piperidinomethyl and 2-piperidinoethyl;

for morpholino-(1–4C)alkyl: morpholinomethyl and 2-morpholinoethyl;

for piperazin-1-yl-(1–4C)alkyl: piperazin-1-ylmethyl and 2-(piperazin-1-yl)ethyl;

for 4-(1–4C)alkylpiperazin-1-yl-(1–4C)alkyl: 4methylpiperazin-1-ylmethyl, 4-ethylpiperazin-1-ylmethyl, 2-(4-methylpiperazin-1-yl)ethyl and 2-(4ethylpiperazin-1-yl)ethyl;

for carboxy-(1–4C)alkyl: carboxymethyl, 1-cboxyethyl, 2-carboxyethyl and 3-carboxypropyl;

for (1–4C)alkoxycarbonyl-(1–4C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbanoyl-(1–4C)alkyl: carbamoylmethyl, 1-carbamoylethyl, 2-carbamoylethyl and 3-carbamoylpropyl;

for N-(1–4C)alkylcarbamoyl-(1–4C)alkyl: N-methylcarbamoylmethyl, N-ethylcarbamoylmethyl, N-propylcarbamoylmethyl, 1-t-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1–4C)alkyl]carbamoyl-(1–4C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;

for (3–4C)alkenylamino: allylamino and methylallylamino;

for (3–4C)alkynylamino: 2-propynylamino and 3-propynylamino;

for di-[(3–4C)alkenyl]amino: diallylamino for di-[(3–4C)alkynyl]amino: di-(2-propynyl)amino;

for 4-(1–4C)alkypiperazin-1-yl: 4-methylpiperazin-1-yl and 4ethylpiperazin-1-yl;

for hydroxy-(2–4C)alkylamino: 2-hydroxyethylamino, 3-hydroxypropylamino and 4-hydroxybutylamino;

for (1–4C)alkoxy-(2–4C)alkylamino: 2-methoxyethylamino, 2-ethoxyethylamino, 3-methoxypropylamino and 3-ethoxypropylamino;

for amino-(2–4C)alkylamino: 2-aminoethylamino, 3-aminopropylamino and 4-aminobutylamino;

for (1–4C)alkylamino-(2–4C)alkylamino: 2-methylaminoethylamino, 2-ethylaminoethylamino, 2-propylaminoethylamino, 3-methylaminopropylamino, 3-ethylaminopropylamino and 4-methylaminobutylamino;

for di-[(1–4C)alkyl]amino-(2–4C)alkylamino: 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino and 4-dimethylaminobutylarnino;

for pyrrolidin-1-yl-(2–4C)alkylamino: 2-(pyrrolidin-1-yl) ethylamino and 3-(pyrrolidin-1-yl)propylamino;

for piperidino-(2–4C)alkylamino: 2-piperidinoethylamino and 3-piperidinopropylamino;

for morpholino-(2–4C)alkylamino: 2-morpholinoethylamino and 3-morpholinopropylamino;

for piperazin-1-yl-(2–4C)alkylamino: 2(piperazin-1-yl) ethylamino and 3-(piperazin-1-yl)propylamino;

for 4-(1–4C)alkylpiperazin-1-yl-(2–4C)alkylamino: 2-(4-methylpiperazin-1-yl)ethylamino and 3(4-methylpiperazin-1-yl)propylamino;

for (2–4C)alkanoylamino: acetamido, propionamido and butyramido;

for (2–4C)alkanoylamino-(2–4C)alkylamino: 2-acetamidoethylamino, 3-acetamidopropylamino and 2-propionamidoethylamino;

for carboxy-(1–4C)alkylamino: carboxymnethylamino, 1-carboxyethylamino, 2-carboxyethylamino and 3-carboxypropylamino; for (1–4C)alkoxycarbonyl-(1–4C)alkylamino: methoxycarbonylmethylamino, ethoxycarbonylmethylamino, 1-methoxycarbonylethylamino, 2-methoxycarbonylethylamino, 2-ethoxycarbonylethylarnino, 2-(tert-butoxycarbonyl)ethylamino and 3-methoxycarbonylpropylamino;

for carbarmoyl-(1–4C)alkylamino: carbamoylmethylaimino, 1-carbamoylethylamino, 2-carbamoylethylamino and 3-carbamoylpropylamino;

for N-(1–4C)alkylcarbamoyl-(1–4C)alkylamino: N-methylcarbamoylmethylamino, N-ethylcarbamoylmethylamino, 2-(N-methylcarbamoyl)ethylamino, 2-(N-ethylcarbamoyl)ethylamino and 3-(N-methylcarbamoyl)propylamino;

for N,N-di-[(1–4C)alkyl]carbamoyl-(1–4C)alkylamino: N,N-dimethylcarbamoylmethylamino, N-ethyl-N-methylcarbamoylmethylamino, N,N-diethylcarbamoylmethylamino, 2-(N,N-dimethylcarbamoyl)ethylamino, 2-(N,N-diethylcarbamoyl)ethylamino and 3-(N,N-dimethylcarbamoyi)propylamino;

for hydroxy-(2–4C)alkoxy: 2-hydroxyethoxy, 3-bydroxypropoxy and 4-hydroxybutoxy;

for (1–4C)alkoxy-(2–4C)alkoxy: 2-methoxyethoxy, 2-ethoxyethoxy, 3-methoxypropoxy and 3-ethoxypropoxy;

for amino-(2–4C)alkoxy: 2-aminoethoxy and 3-aminopropoxy;

for (1–4C)alkylamino-(2–4C)alkoxy: 2-methylaminoethoxy, 2-ethylaminoethoxy, 2-propylaminoethoxy, 3-methylaminopropoxy and 3-ethylaminopropoxy;

for di-[(1–4C)alkyl]amino-(2–4C)alkoxy: 2-dimethylaminoethoxy, 2-(N-ethyl-N-methylamino) ethoxy, 2-diethylaminoetboxy, 2-dipropylaminoethoxy, 3-dimethylaminopropoxy and 3-diethylaminopropoxy;

for pyrrolidin-1-yl-(2–4C)alkoxy: 2pyrrolidin-1-yl-1ethoxy and 3-(pyrrolidin-1-yl)propoxy;

for piperidino-(2–4C)alkoxy: 2-piperidinoethoxy and 3-piperidinopropoxy;

for morpholino-(2–4C)alkoxy: 2-morpholinoethoxy and 3-morpholinopropoxy;

for piperazin-1-yl-(2–4C)alkoxy: 2-(piperazin-1-yl) ethoxy and 34piperazin-1-yl)propoxy;

for 4-(1–4C)alkylpiperazin-1-yl-(2–4C)alkoxy: 2-4-methylpiperazin-1-yl)ethoxy and 3-(4methylpiperazin-1-yl)propoxy.

A suitable value for $R^8$, $Y^1$ or $Y^2$ when it is halogeno or for a halogeno substituent on a phenyl group is, for example, fluoro, chioro, bromo or iodo.

Suitable values for each $R_8$ group include for example:

for (2–4C)alkenyloxy: vinyloxy, allyloxy, methylallyoxy and 2-butenyloxy;

for (2–4C)alkynyloxy: ethynyloxy and 2-propynyloxy;

for (3–4C)alkenyl: allyl, methylallyl, 2-butenyl and 3-butenyl;

for (3–4C)alkynyl: 2-propynyl and 2-butynyl;

for (2–4C)alkanoyl: acetyl, propionyl and butynyl;

for (1–4C)alkoxycarbonyl: methoxycarbonyl, ethoxycarbonyl and tert-butoxycarbonyl;

for N-(1–4C)alkylcarbamoyl: N-methylcarbamoyl and N-ethylcarbamoyl;

for N,N-di-[(1–4C)alkyl]carbamoyl: N,N-dimethylcarbamoyl and N,N-diethylcarbamoyl.

A suitable value for $Y^1$ or $Y^2$ when it is (1–4C) alkanesulphonyloxy is, for example, methanesulphonyloxy, ethanesulphonyloxy or propanesulphonyloxy; when it is, for example, phenyl-(1–4C)alkanesulphonyloxy is, for example, phenylmehanesulphonyloxy or 2-phenylethanesulphonyloxy.

It will be appreciated that, when it is stated that a heterocyclic group in $R^1$, $R^2$ or $R^3$ may optionally be substituted, the heterocyclic groups include those specified in the definitions of $R^1$, $R^2$ and $R^3$ such as, for example, a pyrrolidin-1-yl, morpholino, piperidino-(1–4C)alkyl, piperazin-1-yl-(2–4C)alkylamino or 4-(1–4C)alkylpiperazin-1-yl-(2–4C)alkoxy group.

A suitable pharmaceutically-acceptable salt of an anti-tumour agent of the invention is, for example, an acid-addition salt of an anti-tumour agent of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an anti-tumour of the invention which is sufficiently acidic is an alkali metal salt, for example a sodium or potassium salt, an alkaline earth metal salt, for example a calcium or magnesium salt, an anmmonium salt or a salt with an organic base which affords a physiologically-acceptable cation, for example a salt with methylamine, dimethylamine, trimethylamine, piperidine, morpholine or tris-(2-hydroxyethyl)amine.

Particular novel anti-tumour agents of the invention include, for example, compounds of the formula I, or pharmaceutically-acceptable salts thereof, wherein:

(a) $R^1$, $R^2$ or $R^3$ is independently hydrogen, (1–4C)alkyl, (1–4C)alkenyl, (3–4C)alkynyl, hydroxy-(1–4C)alkyl, (1–4C)alkoxy-(1–4C)alkyl, amino-(1–4C)alkyl, (1–4C)alkylamino-(1–4C)alkyl, di-[(1–4C)alkyl] amino-(1–4C)alkyl, pyrrolidin-1-yl-(1–4C)alkyl, piperidino-(1–4C)alkyl, morpholino1–4C)alkyl, piperazin-1-yl-(1–4C)alkyl, 4-(1–4C)alkylpiperazin-1-yl-(1–4C)alkyl, carboxy-(1–4C)alkyl, (1–4C) alkoxycarbonyl-(1–4C)alkyl, carbamoyl-(1–4C)alkyl, N-(1–4C)alkylcarbamoyl-(1–4C)alkyl or N,N-di-[(1–4C)alkyl]carbamoyl-(1–4C)alkyl, provided that at least one of $R^1$, $R^2$ or $R^3$ is other than hydrogen; and each of $R^4$, $R^5$, $R^6$, $R^7$, $R^8$, m, X, $Y^1$ and $Y^2$ has any of the meanings defined hereinbefore or in this section relating to particular novel anti-tumour agents of the invention;

(b) $R^1$, $R^2$ or $R^3$ is independently amino, (1–4C) alkylamino, (3–4C)alkenylamino, (3–4C) alkynylamino, di-[(1–4C)alkyl]amino, di-[(3–4C) alkenyl]amino, di-[(3–4C)alkynyl]amino, pyrrolidin-1-yl, piperidino, morpholino, piperazin-1-yl, 4-(1–4C) alkylpiperazin-1-yl, hydroxy-(2–4C)alkylamino, (1–4C)alkoxy-(2–4C)alkylamino, amino-(2–4C) alkylamino, (1–4C)alkylamino-(2–4C)alkylanino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, poperazin-1-yl-(2–4C) alkylamino. 4-(1–4C)alkkylpoperazin-1-yl-(2–4C) alkylamino, (2–4C)alkanoylamino, (2–4C) aklanoylamino-(2–4C)alkylamino, carboxy-(1–4Calkylamino, (1–4C)alkoxycarbonyl-(1–4C) alkylamino, carbamoyl(1–4C)alkyamino, N-(1–4C) alkycarbamoyl-(1–4C)alkylamino or N,N-di-[(1–4C) alkyl]carbamoyl-(1–4C)alkylamino; and each of $R^4$, $R^5$, $R^6$, $R^7$, $R^8$, m, X, $Y^1$ and $Y^2$ has any of the meanings defined hereinbefore or in this section relating to particular novel anti-tumour agents of the invention;

(c) $R^1$, $R^2$ or $R^3$ is independently (1–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy or 4-(1–4C)alkylpiperazin-1-yl-(2–4C)alkoxy; and each of $R^4$, $R^5$, $R^6$, $R^7$, $R^1$, m, X, $Y^1$ and $Y^2$ has any of the meanings defined hereinbefore or in this section relating to particular novel anti-tumour agents of the invention;

(d) no more than two of $R^1$, $R^2$ and $R^3$ has any of the meanings defined in paragraph (b) hereinbefore; and each of $R^4$, $R^5$, $R^6$, $R^7$, $R^8$, m, X, $Y^1$ and $Y^2$ has any of the meanings defined hereinbefore or in this section relating to particular novel anti-tumour agents of the invention;

(e) no more than one of $R^1$, $R^2$ and $R^3$ has any of the meanings defined in paragraph (b) hereinbefore; and each of $R^4$, $R^5$, $R^6$, $R^7$, $R^8$, m, X, $Y^1$ and $Y^2$ has any of the meanings defined hereinbefore or in this section relating to particular novel anti-tumour agents of the invention;

(f) each of $R^4$ and $R^5$ is independently methyl, ethyl, propyl or isopropyl and each of $R^1$, $R^2$, $R^3$, $R^6$, $R^7$, $R^8$, m, X, $Y^1$ and $Y^2$ has any of the meanings defined hereinbefore or in this section relating to particular novel anti-tumour agents of the invention;

(g) $R^6$ is hydrogen, methyl, ethyl, propyl or isopropyl and $R^7$ is hydrogen or methyl; and each of $R^1$, $R^2$, $R^3$, $R^4$, $R^5$, $R^8$, m, X, $Y^1$ and $Y^2$ has any of the meanings defined hereinbefore or in this section relating to particular novel anti-tumour agents of the invention;

(h) m is 1 or 2 and each $R^8$ is independently hydrogen, halogeno, hydroxy, (1–4C)alkoxy, (1–4C)alkyl, amino, (1–4C)alkylamino, di-[(1–4C)alkyl]amino or cyano; and each of $R^1$, $R^2$, $R^3$, $R^4$, $R^5$, $R^6$, $R^7$, X, $Y^1$ and $Y^2$ has any of the meanings defined hereinbefore or in this section relating to particular novel anti-tumour agents of the invention;

(i) m is 1 and $R^8$ is hydrogen, halogeno, hydroxy, (1–4C)alkoxy, (1–4C)alkyl, amino, (1–4C)alkylamino, di-[(1–4C)alkyl]amino or cyano; and each of $R^1$, $R^2$, $R^3$, $R^4$, $R^5$, $R^6$, $R^7$, X, $Y^1$ and $Y^2$ has any of the meanings defmned hereinbefore or in this section relating to particular novel anti-tumour agents of the invention;

(j) each of $Y^1$ and $Y^2$ is halogeno or each of $Y^1$ and $Y^2$ is (1–4C)alkanesulphonyloxy, benzenesulphonyloxy or phenyl-(1–4C)alkanesulphonyloxy; and each of $R^1$, $R^2$, $R^3$, $R^4$, $R^5$, $R^6$, $R^1$, $R^8$, m and X, has any of the meanings defined hereinbefore or in this section relating to particular novel anti-tumour agents of the invention.

A preferred compound of the invention is an anti-tumour agent of the formula I wherein each of $R^1$, $R^2$ and $R^3$ is independently hydrogen, methyl, ethyl, propyl, allyl, methylallyl, 2-hydroxyethyl, 3-hydroxypropyl, 2-methoxyethyl, 2-ethoxyethyl, 3-methoxypropyl, 3-ethoxypropyl, 2-carboxyethyl, 3-carboxypropyl, 2-methoxycarbonylethyl, 2-ethoxy-5 carbonylethyl, 3-methoxycarbonylpropyl, 3-ethoxycarbonylpropyl, 2-1-methylcarbamoyl)-ethyl, 3-N-methylcarbamoyl)propyl, 2(N,N-dimethylcarbamoyl)ethyl, 3-(N,N-dimethylcarbamoyl)propyl, methylamino, ethylamino, propylamino, isopropylamino, allylamino, 2-hydroxyethylamino, 3-hydroxypropylamino, 2-methoxyethylamino, 3-methoxypropylamino, 2-aminoethylamino, 3-aminopropylamino, 2-methylaminoethylamino, 3-methylaminopropylamino, 2-ethylaminoethylamino, 3-ethylaminopropylamino, 2-dimethylaminoethylamino, 2-diethylaminoethylamino, 3-dimethylaminopropylamino, 3iethylaminopropylamino, 2-(pyrrolidin-1-yl)ethylamino, 3-(pyrrolidin-1-yl)propylanino, 2-piperidinoethylamino, 3-piperidinopropylamino, 2-morpholinoethylanino, 3-morpholinopropylamino, 2-(piperazin-1-yl)ethylamino, 15 3-(piperazin-1-yl)propylamino, 2-(4-methylpiperazin-1-yl)ethylamino, 3-(4-methylpiperazin-1-yl)propylamino, 2-acetamidoethylamino, 2-propionamidoethylamino, 3-acetamidopropylamino, 3-propionamidopropylamino, 2-carboxyethylamino, 3-carboxypropylamino, 2-methoxycarbonylethylamino, 2-ethoxycarbonylethylamino, 2-(tert-butoxycarbonyl)ethylamino, 3-methoxycarbonylpropylamino, 3-ethoxycarbonylpropylamino, 3-(tert-butoxycarbonyl)propylamino, methoxy or ethoxy; each of $R^4$ and $R^5$ is independently methyl, ethyl, propyl or isopropyl;

$R^6$ is hydrogen, methyl, ethyl, propyl or isopropyl;
$R^7$ is hydrogen or methyl;

X is oxygen;

m is 1 or 2 and each $R^8$ is independently hydrogen, fluoro, chloro, bromo, methoxy, ethoxy, methyl, ethyl, propyl, isopropyl or cyano; and each of $Y^1$ and $Y^2$ is independently chloro, bromo, iodo, methanesulphonyloxy, benzenesulphonyloxy or phenylmethanesulphonyloxy;

or a pharmaceutically-acceptable salt thereof; provided that at least one of $R^1$, $R^2$ and $R^3$ is other than hydrogen and provided that no more than two of $R^1$, $R^2$ and $R^3$ is a substituted amino group (such as methylamino, 2-morpholinoethylamino or 2-acetamidoethylamino).

A fuirther preferred compound of the invention is an anti-tumour agent of the formula I wherein $R^1$ is hydrogen, methyl, ethyl, propyl, allyl, methylallyl, 2-hydroxyethyl, 3-hydroxypropyl, 2-methoxyethyl, 3-methoxypropyl, 3-ethoxypropyl, 2-methoxycarbonylethyl, 2-ethoxycarbonylethyl, 3-methoxycarbonylpropyl, 3-ethoxycarbonylpropyl, 2-(N-methylcarbamoyl)ethyl, 3-(N-methylcarbamoyl)propyl, 2-(N,N-dimethylcarbamoyl)ethyl, 3-(N,N-dimethylcarbamoyl)propyl, methylamino, ethylamino, propylamino, isopropylamino, allylamino, 2-hydroxyethylamino, 3-hydroxypropylamino, 2-methoxyethylamino, 3-methoxypropylamino, 2-aminoethylarnino, 3-aminopropylamino, 2-methylaminoethylamino, 3-methylarinopropylamino, 2-ethylaminoethylamino, 3-ethylaminopropylamino, 2-dimethylaminoethylamino, 2-diethylaminoethylarnino, 3-dimethylaminopropylamino, 3-diethylaminopropylarnino, 2-(pyrrolidin-1-yl)ethylamino, 3-(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4methylpiperazin-1-yl)-ethylamino, 3-(4-methylpiperazin-1-yl)propylamino, 2-acetamidoethylamino, 2-propionamidoethylamino, 3-acetamidopropylamino, 3-propionamidopropylamino, 2-methoxycarbonylethylamino, 2-ethoxycarbonylethylamino, 2-(tert-butoxycarbonyl)ethylamino, 3-methoxycarbonylpropylamino, 3-ethoxycarbonylpropylamino, 3-(tert-butoxycarbonyl)propylamino, methoxy or ethoxy;

$R^2$ is hydrogen, methyl, ethyl, propyl, isopropyl, butyl, allyl, methyl allyl, methoxy or ethoxy;

$R^3$ is hydrogen, methyl, ethyl, propyl, isopropyl, butyl, allyl, methyallyl, methoxy or ethoxy;

$R^4$ is methyl, ethyl, propyl or isopropyl;
$R^5$ is methyl, ethyl, propyl or isopropyl;
$R^6$ is hydrogen, methyl, ethyl, propyl or isopropyl;
$R^7$ is hydrogen or methyl;
X is oxygen;

m is 1 or 2 and each $R^8$ is independently hydrogen, fluoro, chloro, bromo, methoxy, ethoxy, methyl, ethyl, propyl or isopropyl;

$Y^1$ is chloro, bromo, iodo or methanesulphonyloxy; and
$Y^2$ is chloro, bromo, iodo or methanesulphonyloxy;
or a pharmaceutically-acceptable salt thereof; provided that at least one of $R^1$, $R^2$ and $R^3$ is other than hydrogen.

A further preferred compound of the invention is an anti-tumour agent of the formula I wherein $R^1$ is hydrogen, methyl, ethyl, propyl, allyl, 2-methoxyethyl, methylamino, ethylamino, propylamino, isopropylamino, allylamino, 2-dimethylaminoethylamino, 2-diethylaminoethylamino, 2-(pyrrolidin-1-yl)ethylamino, 2-piperidinoethylamino, 2-morpholinoethylamino, 2-(piperazin-1-yl)ethylaniino, 2-(4-methylpiperazin-1-yl)ethylamino, 2-acetamidoethylamino, methoxy or ethoxy;

$R^2$ is hydrogen, methyl, ethyl, propyl, allyl, methoxy or ethoxy;

$R^3$ is hydrogen, methyl, ethyl, propyl, isopropyl, allyl, methoxy or ethoxy;

$R^4$ is methyl or ethyl;

$R^5$ is methyl or ethyl;

$R^6$ is hydrogen, methyl or ethyl;

$R^7$ is hydrogen;

X is oxygen;

m is 1, $R^1$ is located meta to X and $R^8$ is hydrogen, fluoro, chloro, methyl, ethyl, propyl or isopropyl; and each of $Y^1$ and $Y^2$ is chloro, bromo or iodo;

or a pharmaceutically-acceptable salt thereof; provided that at least one of $R^1$, $R^2$ and $R^3$ is other than hydrogen.

A further preferred compound of the invention is an anti-tumour agent of the formula I wherein $R^1$ is hydrogen, methyl, 2-methoxyethyl, isopropylamino, 2-morpholinoethylamino, 2-acetamidoethylamino or methoxy;

$R^2$ is hydrogen, methyl, allyl or methoxy;

$R^3$ is methyl, ethyl, propyl or allyl;

each of $R^4$ and $R^5$ is methyl;

$R^6$ is hydrogen or methyl;

$R^7$ is hydrogen;

X is oxygen;

m is 1 and $R^1$ is hydrogen; and each of $Y^1$ and $Y^2$ is chloro;

or a pharmaceutically-acceptable salt thereof

A specific preferred compound of the invention is the following anti-tumour agent of the formula I:

4-[bis(2-chloroethyl)amino]phenyl 3-[2-(2-acetamidoethylamino)-3-methoxy-5-methyl-1,4-benzoquinonyl]-3-methylbutyrate, 4-[bis(2-chloroethyl)amino]phenyl 3-[2-(2-methoxyethyl)-3,5-dimnethyl-1,4-benzoquinonyl]-3-methylbutyrate, 4-[bis(2-chloroethyl)amino]phenyl 3-(3-allyl-2,5-dimethyl-1,4-benzoquinonyl)-3-methylbutyrate, 4-[bis(2-chloroethyl)amino]phenyl 3-methyl-3-(2,3,5-trimethyl-1,4-benzoquinonyl)butyrate, 4-[bis(2-chloroethyl)amino]phenyl 3-(2,5-dimethyl-1,4-benzoquinonyl)-3-methylbutyrate, 4-[bis(2-chloroethyl)amino]phenyl 3-[3-methoxy-5-methyl-2-(2-morpholinoethylamino)-1,4-benzoquinonyl]-3-methylbutyrate or 4-[bis(2-chloroethyl)amino]phenyl 2,3-dimethyl-3-(2,3,5-trimethyl-1,4-benzoquinonyl)butyrate;

or a pharmaceutically-acceptable salt thereof.

It is an object of a further aspect of the present invention to provide a group of novel (1,4-benzoquinonyl)alkanoic acid derivatives which possesses balanced reduction potentials i.e. reduction potentials which are neither too low such that the rate of reduction of the 1,4-benzoquinonyl group is substantially slowed and nor are they too high such that a significant amount of reduction occurs outwith the hypoxic region of the tumour mass.

According to this aspect of the present invention there is provided an anti-tumour agent of the formula I, or a pharmaceutically-acceptable salt thereof, as defined hereinbefore wherein the reduction potential of the compound is in the range, for example, −200 to −500 mV, preferably in the range, for example, −200 to −475 mV, more preferably in the range, for example, −250 to −450 mV.

The methodology used to measure the reduction potentials of the compounds of the invention is described in detail hereinafter.

An anti-tumour agent of the formula I, or a pharmaceutically-acceptable salt thereof, may be prepared by any process known to be applicable to the preparation of chemically related compounds. According to a further feature of the invention there are provided the processes defined hereinafter for the preparation of an anti-tumour agent of the formula I, or a pharmaceutically-acceptable salt thereof, in which, unless otherwise stated, each of $R^1$, $R^2$, $R^3$, $R^4$, $R^5$, $R^6$, $R^7$, $R^8$, m, X, $Y^1$ and $Y^2$ have any of the meanings defined hereinbefore. Necessary starting materials may be obtained by standard procedures of organic chemistry. The preparation of such starting materials is described hereinafter within the accompanying Examples. Alternative necessary starting materials are obtainable by analogous procedures to those illustrated and such analogous procedures are achievable using the ordinary skill of an organic chemist.

According to this aspect of the invention there is provided a process for the preparation of an anti-tumour agent of the formula I, or a pharmaceutically-acceptable salt thereof, as defined hereinbefore which comprises: the reaction of an acid of the formula II

II wherein each of $R^1$, $R^2$, $R^3$, $R^4$, $R^5$, $R^6$ and $R^7$ has any of the meanings defined hereinbefore, a reactive derivative thereof, with a compound of the formula III

III wherein each of X, $R^8$, m, $Y^1$ and $Y^2$ has any of the meanings defined hereinbefore A suitable reactive derivative of an acid of the formula II is, for example, an acyl halide, for example an acyl chloride formed by the reaction of the acid and an inorganic acid chloride, for example thionyl chloride; a mixed anhydride, for example an anhydride formed by the reaction of the acid and a chloroformnate such as isobutyl chloroformate; an active ester, for example an ester formed by the reaction of the acid and a phenol such as pentafluorophenol, an ester such as pentafluorophenyl trifluoroacetate, an alcohol such as 1-hydroxybenzotriazole or a uranium salt such as 2-(1-benzotriazolyl)-1,1,3,3-tetramethyluronium hexafluorophosphate(V); an acyl azide, for example an azide formed by the reaction of the acid and an azide such as diphenylphosphoryl azide; an acyl cyanide, for example a cyanide formed by the reaction of an acid and a cyanide such as diethylpliosphoryl cyanide; or the product of the reaction of the acid and a carbodiimide such as N,N'-dicyclohexylcarbodiimide or 1-(3-dimethylaminopropyl)-3-ethylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium hydride or potassium hydride, or an organometallic base such as an alkyl-lithium, for example lithium di-isopropylamide, or, for example, an organic amine base such as, for example, pyridine, 2,6-lutidine, collidine, 4-dimethylaminopyridine, triethylamine, morpholine or diazabicyclo-[5.4.0]undec-7-ene. The reaction is also preferably carried out in a suitable inert solvent or diluent, for example methylene chloride, acetonitrile, tetrahydrofuran, 1,2-dimthoxyethame, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

Optionally, when there is an amino, alkylamino, hydroxy or carboxy group in $R^1$, $R^2$, $R^3$ or $R^8$, any such group may be protected by a conventional protecting group which may be removed when so desired by conventional means.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting groups. Thus, for example, an acyl group such as an alkanoyl or alkoxycarbonyl group or an aroyl group may be removed, for exanple, by hydroylsis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trirluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or, for example, a benzyl group which may be removed, for example, by hydrogenation over a catalyst such as palladium-on-carbon.

The starting materials of the formula II and III are either commercially available or they may be prepared by standard procedures of organic chemistry. For example, the starting material of the formula II may be prepared by the hydrolysis of a 3,4-dihydrocoumarin of the formula IV.

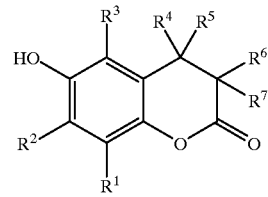

IV wherein each of $R^1$, $R^2$, $R^3$, $R^4$, $R^5$, $R^6$ and $R^7$ has any of the meanings defined hereinbefore, and the subsequent oxidation of the hydroquinone so formed.

Suitable conditions for the hydrolysis and subsequent oxidation reactions for use in the preparation of the starting material of the formula II from a 3,4-dihydrocoumarin of the formula IV include, for example, any agents known in the art for such conversions. For example, the hydrolysis step may be carried out using a suitable base such as an alkali metal hydroxide, for example lithium or sodium hydroxide. If the hydrolysis step is carried out under an atmosphere of air or oxygen, oxidation of the hydroquinone occurs spontaneously. Alternatively the 3,4-dihydrocoumarin may be hydrolysed with water in the presence of an oxidising agent such as an iron halide, for example ferric chloride. In general the reaction is carried out in a suitable inert solvent or diluent, for example water, acetonitrile, N,N-dimethylformamide, methanol or ethanol and at a temperature in the range, for example, 15° to 100° C., conveniently in the range, for example, 20° to 80° C.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out the aforesaid process using an optically active starting material, or by resolution of a racemic form of said compound using a conventional procedure.

As stated hereinbefore the compounds of the formula I of the present invention possess anti-tumour activity, in particular activity by virtue of release of a cytotoxic agent in a hypoxic region of a tumour mass. The cytotoxic and anti-tumour activities of the compounds of the invention may be assessed using, for example, one or more of the procedures set out below.

(a) An in vitro assay which determines the ability of a test compound to cause cross-linking of a piece of DNA using a procedure adapted from the work of Sunter et al., *Biochemical Pharmnacology*, 1992, 44, 59–64. The effects of test compounds were assessed by their ability to cross-link the DNA strands of a linearised $P^{32}$ labelled plasmid. Cross linking was detected by denaturing the DNA and measuring its mobility by gel electrophoresis on a neutral agarose gel. Double- and single-stranded pieces of DNA were separated by molecular size. The detailed methodology was as follows:

PBR322 circular plasmid DNA (Pharmacia Biotech., St. Albans, Hertfordshire, UK) was linearised using Hind III restriction endonuclease and after end-dephosphorylation with alkaline phophatase, T4 polynucleotide kinase (Biolabs, Hitchin, Hertfordshire, UK) was used to add [γ-$^{32}$P]ATP to the 5' ends of the DNA.

Each test compound was dissolved in DMSO and added to a mixture of the plasmid DNA (12.5 ng per assay) and a pH7.2 buffer comprising 25 mM triethanolamine buffer and 1 mM EDTA. Treatments were either carried out under aerobic conditions (solutions gassed with air) or hypoxic conditions (solutions degassed by overnight bubbling with nitrogen and then maintained in an anaerobic chamber with the addition of a 3- to 10-fold excess of the reducing agent sodium dithionite) for up to 3 hours at a temperature in the range of 30° to 37° C. The reaction was stopped by the addition of an ice-cold mixture of 0.6M sodium acetate, 20 mM EDTA and 100 μg/mg tRNA (Sigma, Poole, Dorset, UK). The DNA was precipitated by the addition of 95% ethanol, isolated and stored at −20° C. overnight.

Each plasmid DNA sample was re-suspended in a mixture of 30% aqueous DMSO and 1 mM EDTA and denatured by heating to 90° C. for 2 minutes. The denatured DNA sample was mixed with a pH8.0 buffer comprising 20% Ficoll 400 (Sigma, Poole, Dorset, UK), 0.1M EDTA and 0.25% bromophenol blue and applied to an electrophoresis gel (0.8% agarose in pH8.2 tris-borate-EDTA buffer). Each gel was polarised at 30 volts (3 v/cm) for 3 hours or until the bromophenol dye reached the end of the gel. The gel was dried and the single- and double-stranded DNA was quantified using a phosphoimager (Molecular Dynamics Limited, Kemsing, England). Standard samples of single- and double-stranded DNA were run on each gel and the percentage of double-stranded DNA in the test sample was calculated. Dose response curves were constructed using various concentrations of each test compound to allow the determination of the test dose that produced 50% of double-stranded DNA.

(b) An in vitro assay which determines the ability of a test compound to inhibit the growth of T18 murine breast cancer cells in cell culture under oxic conditions. The cells were grown in monolayer in 96 well plates and treated with compounds for 2 hours under an atmosphere of 90% air and 10% $CO_2$. The cells were then grown on for 6 days at which time the extent of proliferation was assessed using a 3-(4,5-dimethylthiazol-2-yl)-2,5-diphenyltetrazolium bromide (MTT) endpoint. The test is similar to that described in *J. Immunological Methods*, 1983, 65, 55–63. The detailed methodology was as follows.

T18 murine breast tumour cells (derived from a spontaneous mammary tumour in the Balb/c mouse colony at Zeneca Pharmaceuticals, Mereside, Macclesfield, UK) were harvested from an exponentially growing monolayer culture. The cells were counted, diluted in RPMI 1640 culture medium (Gibco BRL, Life Technologies, Paisley, UK; supplemented with 15% foetal calf serum, glutamine, pyruvate, penicillin and streptomycin), and transferred to 96 well plates at 500 cells per 50 μl per well. The cells were incubated at 37° C. in a $CO_2$ incubator (i.e. under an atmosphere of 90% air and 10% $CO_2$) for 2 days. Further fresh culture medium (125 μl) was added to each well. Each test compound was dissolved in DMSO and diluted to the required test concentration in water. A 25 μl portion of each test solution was added to each well. The plates were then returned to the incubator for 2 hours. At the end of this time, the supernatant culture medium containing the test compound was removed. The residual cells in each well were washed once with 200 μl of phosphate buffered saline (PBSA) and fresh culture medium (200 μl) was added. The plates were then returned to the $CO_2$ incubator and grown on for 6 days. A 50 μl portion of MTT (5 mg/ml) was added to each well and the plates were incubated for a further 4 hours, during which time viable cells converted MTT into an insoluble, intracellular deposit of blue formazan, the extent of conversion being proportional to the number of viable cells in the well. The supernatant culture medium containing excess MTT was removed and DMSO (100 μl) was added to solubilise the formazan, the concentration of which was measured by determining the optical density at 540 nM. Various concentrations of each test compound were assayed to allow the determination of the concentration causing 50% inhibition ($IC_{50}$).

(c) An in vitro assay which determines the ability of a test compound to inhibit the growth in an oxygenated culture medium of spheroidal aggregates (~400 microns in diameter) of EMT6 murine breast cancer cells. As the oxygen diffusion distance through tissue is approximately 120–150 microns, such spheroids have a chronically hypoxic central population of cells and a well oxygenated outer layer of cells. The multicellular spheroids were treated with test compounds for 2 hours as a well oxygenated suspension culture. The spheroids were subsequently washed free of test compound and selected spheroids were transferred to static culture so that the effect of treatment on volume growth could be measured. The detailed methodology was as follow:

EMT6 murine breast cells (obtained from P. R. Twentyman, MRC Oncology and Radiotherapeutics Unit, Cambridge, UK) were harvested from exponentially growing monolayer cultures and approximately 1×10$^6$ cells were used to inoculate a 500 ml spinner culture vessel containing Eagles minimal essential medium (200 ml; supplemented with 10% foetal calf serum, glutamate, non-essential amino acids, penicillin and streptomycin). The spinner vessel was gassed with a mixture of 90% air and 10% $CO_2$, sealed, and incubated at 37° C. for 4–5 days with slow stirring (50 rpm for the first 24 hours and thereafter 40 rpm). The cells aggregated into clumps which grew into tight spheroids with a mean diameter of about 400 microns. Aliquots (5 ml) of spheroid-containing culture medium were transferred to conical flasks (siliconised, 25 ml) which were gassed with a mixture of 90% air and 10% $CO_2$ and sealed with a rubber stopper. The flasks were placed in an orbital shaker in a $CO_2$ incubator at 37° C. and gently agitated for at least 15 minutes. Each test compound was dissolved in DMSO and diluted to the required test concentration in water. A 200 μl portion of each test solution was added by syringe to each sealed flask. The resultant mixtures were incubated for 2 hours, each transferred to a centrifuge tube and allowed to settle. The supernatant culture medium containing the test compound was decanted and fresh culture medium (5 ml) was added to each tube The contents of each tube were then transferred to plastic petri dishes (35 mm diameter) and observed under a dissecting microscope with a calibrated graticule. From each treatment group, 6 spheroids of uniform shape and approximately 400 micron diameter were selected and transferred to separate wells in a 24-well plate, to each well of which had been added 1% agar (0.3 ml; to create a base layer that prevents spheroid attachment) and 1 ml of culture medium. The area of each spheroid was measured using an image analyser and the 24-well plates were transferred to a $CO_2$ incubator at 37° C. The spheroids were then re-measured every 2–3 days for up to 21 days, with fresh culture medium (250 μl) being added to each well every 3 days. The spheroid volumes were calculated from the area measurements (assuming spherical shape) and volume growth curves were constructed from which the effect of treatment could be assessed. The test dose which caused stasis (no growth or regression of spheroid size) during a period of 2–3 weeks was noted.

(d) An in vivo assay in a group of Balb/c mice which determines the ability of a test compound to delay the growth of T18 murine breast tumours. The detailed methodology was as follows:

T18 murine breast tumour tissue was routinely maintained by animal to animal passage. To prepare a batch of tumours for an experiment, tumour tissue was removed from several donor Balb/c mice and placed in saline. Outer tissue was removed and healthy looking regions of tumour were cut into approximately 1 mm pieces and implanted subcutaneously by trocar into the left flanks of anaesthetised female Balb/c mice. After 2–3 weeks, most of the implants had grown to approximately 8 mm in diameter. The animals were placed randomly into groups of 6–7, rejecting any with very large, or small, tumours. Each test compound was dissolved in DMSO and diluted with Cremophor EL followed by saline, to give a 1:1:3 mixture of DMSO, Cremophor EL and saline. Each test compound was administered by the intraperitoneal route as a single bolus dose (0.1 ml per 10 g body weight of each animal). Control animals received vehicle alone. All mice were weighed daily and the dimensions (length and width) of each tumour were measured every 2–3 days using vernier calipers. The measurements were used to estimate the volume of each tumour assuming a prolate elipsoid shape (volume=$\pi/6 \times Length \times Width^2$). Growth curves were constructed and the effect of treatment was assessed using a growth delay endpoint.

Although the pharmacological properties of the compounds of the formula I vary with structural change as expected, in general activity possessed by compounds of the formula I may be demonstrated at the following concentrations or doses in one or more of the above test procedures:

Test (a): under hypoxic conditions, $IC_{50}$ in the range, for example 1–20 μM; under oxic conditions, $IC_{50}$ generally greater than three-fold higher;

Test (b): $IC_{50}$ in the range, for example, 1–30 μM;

Test (c): for stasis; $ED_{50}$ in the range, for example, 1–6 μM; and

Test (d): a dose in the range, for example, 30–100 mg/kg intraperitoneally gives a growth delay of, for example, 4 to 15 days.

Thus, by way of example, the compound of Example 2 hereinafter has an $IC_{50}$ of 4.8 μM in Test (b), a stasis $ED_{50}$ dose of approximately 6 μM in Test (c) and a growth delay of approximately 12 days from a single bonus dose of approximately 50 mg/kg intraperitoneally in Test (d).

As stated hereinbefore it is an object of one aspect of the present invention to provide double-prodrug compounds which rapidly release a cytotoxic drug when they encounter a region of low oxygen tension such as in the hypoxic region of a solid tumour. This property may be assessed, for example, using the following test procedure:

Each test compound was dissolved in acetonitrile (approximately 2 mg/ml) and diluted in pH7.4 phosphate buffer (if solubility difficulties were encountered, the minimum additional quantity of acetonitrile was added) to give a test concentration of approximately $5 \times 10^{-5}$M. Each test solution was thoroughly degassed under helium and warmed to a thermostatically-controlled reaction temperature of 37° C. A sodium dithionite $Na_2S_2O_4$) solution (100 μl of a 100 mg/ml solution in degassed water) was added to a portion (1.4 ml) of each test solution. Aliquots of the reaction solution were taken at regular intervals and analysed by high performance liquid chromatography (HPLC) for release of the cytotoxic drug moiety and formation of the appropriate 3,4-dihydrocoumarin. Typical HPLC conditions involved use of a SSODSl reversed-phase column (250 by 4.6 mm, packed with 5 micron octadecylsilane-coated Spherisorb particles from Jones Chromatography, Hengoed, Glamorgan, UK) using a 75:25:0.1 mixture of acetonitrile, water and trifluoroacetic acid as eluent and a flow rate of 1.5 ml per minute.

In general, it was found that, under reductive conditions, the compounds of the invention of the formula I rapidly released the cytotoxic drug moiety with a $t_{1/2}$ of less than 2 hours, preferably less than 1 hour, more preferably less than 20 minutes and especially less than 10 minutes. In general, it was found that reductive conditions caused the release of the cytotoxic drug moiety so rapidly that the hydroquinone product of the reduction step could not be detected. In such instances the $t_{1/2}$ of cytotoxic drug release was substantially less than 10 minutes.

As stated hereinbefore it is a further object of another aspect of the present invention to provide double-prodrug compounds which possess a balanced reduction potential i.e. a reduction potential that is not so high that a significant proportion of reduction occurs outwith areas of low oxygen tension, nor so low that a significant proportion of reduction does not occur even in an area of low oxygen tension. The reduction potential of the compounds of the present invention may be assessed, for example, using the following test procedure:

Each test compound (2 mg) was dissolved in DMF and cyclic voltammetry was carried out using a Luggin Cell fitted with platinum working and secondary electrodes and a standard saturated calomel reference electrode (SCE) and tetra-butylammonium bromide (0.1 moles per litre in DMF) as electrolyte (see, for example, G. A. Mabbott, *J Chem. Ed.*, 1983, 60 697 and J. G. Dick et al., Metrohin Monographs, Electrode Reaction Kinetics determined by Cyclic Sweep Triangular Wave Voltammetry, 1983). In a typical experiment, for example, the potential of the working electrode, controlled relative to the reference electrode, was scanned at 100 mV per second from the starting potential to the switching potential and back to the initial potential. The current produced was plotted as a function of potential and the cathodic peak potential (Epc) was taken as a measure of the reduction potential in DMF solution. An Eaq value for each test compound in aqueous solution was determined by way of a calibration plot based on measured Epc values of DMF solutions of a group of standard quinone compounds for which the pH7 Eaq values in aqueous solutions were known (P. Wardman, *J. Phys. Chem. Ref Data*, 1989 18, 1637). The calibration plot allowed the following equation to be determined:

$$Eaq\ (V) = 1.23\ Epc\ (V) + 0.62$$

In general, the compounds of the invention of the formula I have a calculated Eaq value in the range, for example, −200 to −500 mV, preferably in the range, for example, −200 to −475 mV, more preferably in the range, for example, −250 to −450 mV.

According to a further aspect of the invention there is provided a pharmaceutical composition which comprises an anti-tumour agent of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parental injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The anti-tumour agent will normally be administered to a warm-blooded animal at a unit dose within the range 50–10000 mg per square meter body area of the animal, i.e. approximately 1–200 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily by varied depending upon the host treated, the particular route of administration, and the severity of the illness being treated. Accordingly the optimum dosage may be determined by the practitioner who is treating any particular patient.

According to a further aspect of the present invention there is provided an anti-tumour agent of the formula I as defined hereinbefore for use in a method of treatment of the human or animal body by therapy.

We have found that the compounds of the present invention possess anti-poliferative properties such as anti-tumour properties which are believed to arise from the hypoxia-selective release of a cytotoxic agent from the double-prodrug of the formula I. Accordingly the compounds of the present invention are expected to be useful in the treatment of tumours of sufficient size to possess hypoxic regions such that reduction of the 1,4-benzoquinonyl moiety occurs and the cytotoxic moiety is thereafter rapidly released.

It will be appreciated by the person skilled in the art that the above-mentioned anti-proliferative activity of the compounds of the present invention against spheroidal aggregates of EMT6 murine breast cancer cells demonstrates not only that the compounds of the present invention are hypoxia-selective prodrugs of a cytotoxic agent but also that the cytotoxic agent, once released, can diffuse into nearby oxic regions of the celluar aggregate to continue the destruction of cancer cells. Hence sufficient cytotoxic activity can be released to cause stasis of the growth of the spheroidal aggregate of cancer cells.

Thus according to this aspect of the invention there is provided the use of an anti-tumour agent of the formula I, or a pharmaceutically-acceptable salt thereof, as defined hereinbefore in the manufacture of a medicament for use in the production of an anti-proliferative effect in a warm-blooded animal, such as man.

According to a further feature of this aspect of the invention there is provided a method for producing an anti-proliferative effect in a warm-blooded animal, such as man, in need of such treatment which comprises administering to said animal an effective amount of an anti-tumour agent of the formula I, or a pharmaceutically-acceptable salt thereof, as defined hereinbefore.

As stated above the size of the dose required for the therapeutic or prophylactic treatment of a particular proliferative disease will necessarily by varied depending on the host treated, the route of administration and the severity of the illness being treated. A unit dose in the range, for example, 1–200 mg/kg, preferably 1–100 mg/kg, more preferably 1–10 mg/kg is envisaged.

The anti-tumour effect of the compounds of the present invention may be applied as a sole therapy or may involve, in addition, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer such as a combination of surgery, radiotherapy and/or chemotherapy. In particular, it is known that irradiation or treatment with antiangiogenic and/or vascular permeability reducing agents can enhance the amount of hypoxic tissue within a tumour. Therefore the effectiveness of the compounds of the present invention is expected to be improved by conjoint treatment with radiotherapy and/or with an antiangiogenic agent.

In general such chemotherapy may cover three main categories of therapeutic agent:

(i) antiangiogenic agents including those believed to act by way of inhibition of vascular endothelial growth factor (VEGF) such as the compounds disclosed in International Patent Applications WO 97/22596, WO 97/30035 and WO 97/32856 and antiangiogenic agents that work by different mechanisms, for example linomide, inhibitors of integrin $\alpha v \beta 3$ function, angiostatin, razoxin and thalidomide;

(ii) cytostatic agents such as antioestrogens (for example tamoxifen, toremifene, raloxifene, droloxifene and iodoxyfene), progestogens (for example megestrol acetate), aromatase inhibitors (for example anastrozole, letrazole, vorazole and exemestane), antiprogestogens, antiandrogens (for example flutarnide, nilutamide, bicalutamide and cyproterone acetate), LHRH agonists and antagonists (for example goserelin acetate, luprolide and buserelin), inhibitors of testosterone 5$\alpha$-dihydroreductase (for example finasteride), anti-invasion agents (for example metalloproteinase inhibitors like marimastat and inhibitors of urokinase plasminogen activator receptor function) and inhibitors of growth factors (for example inhibitors of epidermal growth factor (EGF), fibroblast growth factor (FGF), platelet derived growth factor and hepatocyte growth factor such as EGF receptor tyrosine kinase inhibitors and serine/threonine kinase inhibitors); and (iii) antiproliferative, antineoplastic drugs and combinations thereof, as used in medical oncology, such as antimetabolites (for example antifolates like methotrexate and raltitrexed, fluoropyrimidines like 5-fluorouracil, purine and adenosine analogues and cytosine arabinoside); antitumour antibiotics (for example the bleomycins and anthracyclines like doxorubicin, daunomycin, epirubicin and idarubicin, mitomycin-C, dactinomycin and mithramycin); platinum derivatives (for example cisplatin and carboplatin); alkylating agents (for example nitrogen mustard, melphalan, chlorambucil, busulphan, cyclophosphamide, ifosfamide, nitrosoureas and thiotepa); antimitotic agents (for example vinca alkaloids like vincrisitine and taxoids like taxol and taxotere); topoisomerase inhibitors (for example epipodophyllotoxins like etoposide and teniposide, arnsacrine and topotecan).

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) unless otherwise stated, operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Koffler hot plate aparatus.

(vi) the structures of the end-products of the formula I were confirmed by nuclear (generally proton) magnetic resonance (NMR) and mass spectral techniques; proton magnetic resonance chemical shift values were measured on the delta scale and peak mutiplicities are shown as follows: s, singlet; d, doublet; t, triplet; m, multiplet, unless otherwise stated end-products of the formula I were dissolved in $CD_3SOCD_3$ for the determination of NMR values;

(vii) intermediates were not generally fully characterised and purity was assessed by thin layer chromatography (TLC), infra-red (IR) or NMR analysis;

(viii) the following abbreviation have been used:

| | |
|---|---|
| DMF | N,N-dimethylformamide; |
| DMA | N,N-dimethylacetamide; |
| DMSO | dimethylsulphoxide; |
| EDTA | ethylenediaminetetracetic acid. |

EXAMPLE 1

A solution of 1-(3-dimethylaminopropyl)-3-ethylcarbodiimide hydrochloride (0.208 g) in methylene chloride (2 ml) was added to a stirred mixture of 3-(5-allyl-2,3-dimethyl-1,4-benzoquinonyl)-3-methylbutyric acid (0.2 g), 4-[bis(2-chloroethyl)-amino]phenol hydrochloride (J. Chem. Soc. Perkin Trans. I. 1973, 2397–2402; 0.2 g), 4-dimethylaminopyridine (0.186 g) and methylene chloride (8 ml). The resultant mixture was stirred at ambient temperature for 16 hours. The mixture was evaporated and the residue was purified by column chromatography on silica using a 9:1 mixture of petroleum ether (b.p. 40 to 60° C.) and ethyl acetate as eluent The resultant material was further purified by HPLC using a 92.5 : 7.5 mixture of cyclohexane and ethyl acetate as eluent. There was thus obtained 4-[bis (2-chloroethyl)amino]phenyl 3-(5-allyl-2,3-dimethyl-1,4-benzoquinonyl)-3-methylbutyrate as an oil (0.127 g);

NMR Spectrum: ($CDCl_3$) 1.52 (s, 3H), 1.55 (s, 3H), 1.9 (s, 3H), 1.96 (s, 3H), 3.19 (s, 2H), 3.47 (d, 2H), 3.58 (t, 4H), 3.67 (t, 4H), 5.0 (m, 2H), 5.82 (m, 1H), 6.6 (d, 2H), 6.85 (d, 2H);

Mass Spectrum: $(M+Na^+)$ 518, 516, 514.

The 3-(5-allyl-2,3-dimethyl-1,4-benzoquinonyl)-3-methylbutyric acid used as a starting material was obtained as follows:

A mixture of 6-hydroxy-4,4,7,8-tetramethyl-3,4-dihydrocoumarin (J. Amer. Chem. Soc., 1983, 105. 2752–2760; 5 g), allyl bromide (5.9 ml), potassium carbonate (9.4 g) and DMF (50 ml) was stirred at ambient temperature for 2.5 hours. The mixture was partitioned between diethyl ether and water. The organic phase was washed with a saturated aqueous sodium chloride solution, dried ($MgSO_4$) and evaporated. There was thus obtained 6-allyloxy-4,4,7,8-tetramethyl-3,4-dihydrocoumarin (6 g) which was used without fer purification; NMR Spectrum: ($CDCl_3$) 1.32 (s, 6H), 2.16 (s, 3H), 2.22 (s, 3H), 2.56 (s, 2H), 4.53 (d, 2H), 5.35 (m, 2H), 6.08 (m, 1H), 6.64 (s, 1H).

A mixture of the material so obtained (6 g) and N,N-dimethylaniline (95 ml) was stirred and heated to 200° C. for 4.5 hours. The mixture was evaporated and the residue was purified by column chromatography on silica using a 4:1 mixture of petroleum ether (b.p. 40 to 60° C.) and ethyl acetate as eluent. There was thus obtained 5-allyl-6-hydroxy-4,4,7,8-tetramethyl-3,4-dihydrocoumarin (4.4 g), m.p. 152–154° C.; NMR Spectrum: ($CDCl_3$) 1.43 (s, 6H), 2.18 (s, 3H), 2.23 (s, 3H), 2.54 (s, 2H), 3.57 (d, 2H), 4.93 (s, 2H), 5.22 (m, 2H), 6.1 (m, 1H).

A solution of a portion (2.2 g) of the material so obtained in acetonitrile (22 ml) was stirred and heated to reflux. A solution of ferric chloride hexahydrate (10.8 g) in a mixture of acetonitrile (22 ml) and water (22 ml) was added portionwise and the mixture was heated to reflux for 2 hours. The mixture was cooled to ambient temperature and partitioned between diethyl ether and a 5% aqueous sodium bicarbonate solution. The aqueous phase was acidified by the addition of 2N aqueous hydrochloric acid and extracted with diethyl ether. The resultant organic phase was dried ($MgSO_4$) and evaporated. There was thus obtained 3-(5-allyl-2,3-dimethyl-1,4-benzoquinonyl)-3-methylbutyric acid (0.43 g); NMR Spectrum: ($CDCl_3$) 1.45 (s, 6H), 1.94 (s, 3H), 1.95 (s, 3H), 3.01 (s, 2H), 3.45 (d, 2H), 5.0 (m, 2H), 5.8 (m, 1H).

EXAMPLE 2

Using an analogous procedure to that described in Example 1,3-[2-(2-methoxyethyl)-3,5-dimethyl-1,4-berooquinonyl]-3-methylbutyric acid was reacted with 4-[bis(2-chloroethyl)amino]phenol hydrochloride to give 4-[bis(2-chloroethyl)amino]phenyl 3-[2-(2-methoxyethyl)-3,5-dimethyl-1,4-benzoquinonyl]-3-methylbutyrate as an oil in 55% yield. NMR Spectrum: ($CDCl_3$) 1.52 (s, 6H), 1.97 (s, 3H), 2.15 (s, 3H), 2.7 (t, 2H), 3.2 (s, 2H), 3.22 (s, 3H), 3.35 (t, 2H), 3.6 (t, 4H), 3.68 (t, 4H), 6.6 (d, 2H), 6.86 (d, 2H); Mass Spectrum: $(M+Na^+)$ 536, 534, 532.

The 3-[2-(2-methoxyethyl)-3,5-dimethyl-1,4-benzoquinonyl]-3-methylbutyric acid used as a starting material was obtained as follows:

A solution of 6-hydroxy-4,4,5,7-tetramethyl-3,4-dihydrocoumarin (J. Org. Chem., 1989, 54, 3303; 10.6 g) in acetonitrile (125 ml) was stirred and heated to reflux. A solution of ferric chloride hexahydrate (25 g) in a mixture of acetonitrile (115 ml) and water (115 ml) was added portionwise during 2 hours. The resultant mixture was cooled to ambient temperature and partitioned between diethyl ether and water. The organic phase was extracted with 5% aqueous sodium bicarbonate solution. The aqueous phase was acidified by the addition of 2N aqueous hydrochloric acid and extracted with diethyl ether. The organic phase was dried ($MgSO_4$) and evaporated. The residue was purified by column chromatography on silica using a 1:1:0.02 mixture of petroleum ether (b.p. 40 to 60° C.), diethyl ether and acetic acid as eluent. There was thus obtained 3-methyl-3-(3,5-dimethyl-1,4-benzoquinonyl)butyric acid (3.08 g); NMR Spectrum ($CDCl_3$) 1.44 (s, 6H), 1.99 (s, 3H), 2.17 (s, 3H), 3.05 (s, 2H), 6.45 (s, 1H).

A mixture of 3-methyl-3-(3,5-dimethyl-1,4-benzoquinonyl)butyric acid (6 g), 2-tert-butyl-1,3-diisopropylisourea (20 g) and methylene chloride (100 ml) was stirred at ambient temperature for 16 hours. The mixture was evaporated. Diethyl ether was added and the mixture was filtered. The filtrate was evaporated and the residue was purified by column chromatography on silica using a 6:1 mixture of petroleum ether (b.p. 40 to 60° C.) and ethyl acetate as eluent. There was thus obtained tert-butyl 3-methyl-3-(3,5-dimethyl-1,4-benzoquinonyl)butyrate as an oil (5.97 g); NMR Spectrum: (CDCl$_3$) 1.35 (s, 9H), 1.43 (s, 6H), 1.99 (s, 3H), 2.17 (s, 3H), 2.90 (s, 2H).

A mixture of tert-butyl 3-methyl-3-(3,5-dimethyl-1,4-benzoquinonyl)butyrate (1.5 g), 3-methoxypropionic acid (1.07 g) and silver nitrate (0.873 g) was dissolved in a mixture of acetonitrile (20 ml) and water (20 ml). The mixture was stirred and heated to 75° C. and a solution of sodium persulphate (Na$_2$S$_2$O$_8$; 2.57 g) in water (20 ml) was added over a 30 minute period. The resultant mixture was stirred at 75° C. for a further 30 minutes and then cooled to ambient temperature. The mixture was partitioned between diethyl ether and water. The organic phase was washed with water and with a saturated aqueous sodium chloride solution, dried (MgSO$_4$) and evaporated. The residue was purified by column chromatography on silica using a 9:1 mixture of petroleum ether (b.p. 40 to 60° C.) and ethyl acetate as eluent. There was thus obtained tert-butyl 3-[2-(2-methoxyethyl)-3,5-dimethyl-1,4-benzoquinonyl]-3-methylbutyrate as an oil (0.279 g); NMR Spectrum: (CDCl$_3$) 1.37 (s, 9H), 1.41 (s, 6H), 2.0 (s, 3H), 2.13 (s, 3H), 2.73 (t, 2H), 2.9 (s, 2H), 3.3 (s, 3H), 3.43 (t, 2H).

A mixture of the material so obtained, trifluoroacetic acid (0.6 ml), water (1 drop) and methylene chloride (1.8 ml) was stirred at ambient temperature for 2.5 hours. The mixture was evaporated to give the required starting material in quantitative yield; NMR Spectrum: (CDCl$_3$) 1.43 (s, 6H), 2.0 (s, 3H), 2.15 (s, 311), 2.72 (t, 2H), 3.1 (s, 2H), 3.32 (s, 3H), 3.42 (t, 2H).

EXAMPLE 3

Using an analogous procedure to that described in Example 1, 3-{2-[2-(N,N-dimethylcarbamoyl)ethyl]-3,5imethyl-1,4-benzoquinonyl}-3-methylbutyric acid was reacted with 4-[bis(2-chloroethyl)amino]phenol hydrochloride to give 4-[bis(2-chloroethyl)amino]phenyl 3-{2-[2-(N,N-dimethylcarbamoyl)ethyl]-3,5-dimethyl-1,4-benzoquinonyl}-3-methylbutyrate as an oil in 24% yield; NMR Spectrum: (CDCl$_3$) 1.51 (s, 6H), 1.97 (s, 3H), 2.16 (s, 3H), 2.35 (t, 2H), 2.72 (t, 2H), 2.8 (s, 3H), 2.9 (s, 3H), 3.21 (s, 2H), 3.57 (t, 4H), 3.67 (t, 4H), 6.61 (d, 2H), 6.84 (d, 2H); Mass Srectrum: (M+Na$^+$) 577, 575, 573.

The 3-{2-[2-(N,N-dimethylcarbamoyl)ethyl]-3,5-dimethyl-1,4-benzoquinonyl}-3-methylbutyric acid used as a starting material was obtained as follows:

A mixture of tert-butyl 3-methyl-3-(3,5-dimethyl-1,4-benzoquinonyl)butyrate (1 g), succinic acid (0.809 g) and silver nitrate (0.582 g) was dissolved in a mixture of acetonitrile (13 ml) and water (13 ml). The mixture was stirred and heated to 70° C. and a solution of sodium persulphate (1.71 g) in water (13 ml) was added dropwise. The resultant mixture was heated to 70° C. for a further 10 minutes and then cooled to ambient temperature. The mixture was partitioned between diethyl ether and a saturated aqueous sodium bicarbonate solution. The aqueous phase was acidified to pH2 with 2N aqueous hydrochloric acid and extracted with diethyl ether. The organic extract was washed with water, dried (MgSO$_4$) and evaporated. There was thus obtained tert-butyl 3-[2-(2-carboxyethyl)-3,5-dimethyl-1,4-benzoquinonyl]-3-methylbutyrate as a foam (0.544 g); NMR Spectrum: (CDCl$_3$) 1.37 (s, 9H), 1.4 (s, 6H), 2.01 (s, 3H), 2.14 (s, 3H), 2.5 (t, 2H), 2.76 (t, 2H), 2.91 (s, 2H).

A solution of 1-(3-dimethylaminopropyl)-3-ethylcarbodiimide hydrochloride (0.577 g) in methylene chloride (2 ml) was added to a stirred mixture of tert-butyl 3-[2-(2-carboxyethyl)-3,5-dimethyl-1,4-benzoquinonyl]-3-methylbutyrate (0.73 g), a solution of dimethylamine (4 mmol) in chloroform (1.1 ml), and methylene chloride (10 ml). The resultant mixture was stirred at ambient temperature for 16 hours. The mixture was evaporated and the residue was purified by column chromatography on silica using a 3:2 mixture of petroleum ether (b.p. 40 to 60° C.) and ethyl acetate as eluent. There was thus obtained tert-butyl 3-{2-[2-(N,N-dimethylcarbamoylethyl]-3,5-dimethyl-1,4-benzoquinonyl}-3-methylbutyrate as an oil (0.23 g); NMR Spectrum: (CDCl$_3$) 1.35 (s, 9H), 1.41 (s, 6H), 2.01 (s, 3H), 2.14 (s, 3H), 2.45 (t, 2H), 2.75 (t, 2H), 2.88 (s, 2H), 2.94 (s, 3H), 2.98 (s, 3H).

A mixture of a portion (0.2 g) of the material so obtained, trifluoroacetic acid (0.45 ml), water (1 drop) and methylene chloride (2 ml) was stirred at ambient temperature for 4 hours. The mixture was evaporated to give the required starting material in quantitative yield; NMR Spectrum: (CDCl$_3$) 1.43 (s, 6H), 1.96 (s, 3H), 2.14 (s, 3H), 2.48 (m, 2H), 2.72 (m, 2H), 3.0 (m, 8H).

EXAMPLE 4

Using an analogous procedure to that described in Example 1,3-(5-allyl-2,3-dimethoxy-1,4-benzoquinonyl)-3-methylbutyric acid was reacted with 4-[bis(2-chloroethyl) amino]phenol to give 4-[bis(2-chloroethyl)amino]phenyl 3-(5-allyl-2,3-dimethoxy-1,4-benzoquinonyl)-3-methylbutyrate as an oil in 20% yield; NMR Spectrum: (CDCl$_3$) 1.53 (s, 6H), 3.21 (s, 2H), 3.47 (s, 2H), 3.6 (s, 4H), 3.68 (t, 4H), 3.89 (s, 3H), 3.9 (s, 3H), 5.02 (m, 2H), 5.82 (m, 1H), 6.63 (d, 2H), 6.85 (d, 2H); Mass Spectrum: (M+Na$^+$) 550, 548, 546.

The 3-(5-allyl-2,3-dimethoxy-1,4-benzoquinonyl)-3-methylbutryric acid used as a starting material was obtained as follows:

Sodium hydrosulphite (Na$_2$S$_2$O$_4$, 26 g) was added portionwise to a stirred solution of 2,3-dimethoxy-1,4-benzoquinone (*J. Med. Chem.*, 1971, 14, 45; 5 g) in a mixture of methanol (50 ml) and water (100 ml). The resultant mixture was stirred at ambient temperature for 1 hour. The mixture was partitioned between ethyl acetate and water. The organic phase was dried (MgSO$_4$) and evaporated to give 2,3-dimethoxyhydroquinone (2 g); NMR Spectrum: (CD$_3$SOCD$_3$) 3.71 (s, 6H), 6.37 (s, 2H), 8.47 (s, 2H).

A mixture of 2,3-dimethoxyhydroquinone (3.6 g), methyl 3,3-dimethylacrylate (3.2 ml) and methanesulphonic acid (36 ml) was stirred and heated to 70° C. for 2 hours. The mixture was poured onto a mixture of ice and water and the resultant mixture was extracted with ethyl acetate. The organic phase was washed with a 5% aqueous sodium bicarbonate solution, dried (MgSO$_4$) and evaporated. The residue was purified by column chromatography on silica using a 3:2 mixture of petroleum ether (b.p. 40 to 60° C.) and ethyl cetate as eluent. There was thus obtained 6-hydroxy-7,8-dimethoxy- 4,4-dimethyl-3,4-dihydrocoumarin (2.3 g); NMR Spectrum: (CDCl$_3$) 1.3 (s, 6H), 2.59 (s, 21), 3.95 (s, 6H), 5.58 (s, 1H), 6.64 (s, 1H).

A mixture of 6-hydroxy-7,8-dimethoxy-4,4-dimethyl-3,4-dihydrocoumarin (1.6 g), allyl bromide (1.65 ml), potassium carbonate (2.63 g) and DMF (15 ml) was stirred and heated to 70° C. for 1 hour. The mixture was partitioned between diethyl ether and water. The organic phase was washed with a saturated aqueous sodium chloride solution, dried (MgSO$_4$) and evaporated. The residue was purified by column chromatography on silica using a 3:2 mixture of petroleum ether (b.p. 40 to 60° C.) and diethyl ether as eluent. There was thus obtained 6-allytoxy-7,8-dimethoxy-4,4-dimethyl-3,4-dihydrocoumarin (1.51 g); NMR Spectrum: (CDCl$_3$) 1.31 (s, 6H), 2.59 (s, 2H), 3.9 (s, 3H), 3.95 (s, 3H), 4.57 (d, 2H), 5.37 (m, 2H), 6.08 (m, 1H), 6.58 (s, 1H).

A mixture of the material so obtained and N,N-dimethylaniline (20 ml) was stirred and heated to 200° C. for 4 hours. The mixture was evaporated and the residue was purified by column chromatography on silica using a 1:1 mixture of petroleum ether (b.p. 40 to 60° C.) and diethyl ether as eluent. There was thus obtained 5-allyl-6-hydroxy-7,8-dimethoxy-4,4-dimethyl-3,4-dihydrocoumarin (1.4 g); NMR Spectrum: (CDCl$_3$) 1.44 (s, 6H), 2.56 (s, 2H), 3.58 (m, 2H), 3.91 (s, 3H), 3.97 (s, 3H), 5.02 (m, 2H), 5.73 (s, 1H), 6.02 (m, 1H), A mixture of a portion (0.65 g) of the material so obtained, 2N aqueous sodium hydroxide solution (1 ml) and water (25 ml) was stirred at ambient temperature in air for 1.5 hours. The mixture was extracted with diethyl ether. The organic phase was washed with water and with a saturated aqueous sodium chloride solution, dried (MgSO$_4$) and evaporated. The residue was purified by column chromatography on silica using a 50:50:0.1 mixture of petroleum ether (b.p. 40 to 60° C.), diethyl ether and acetic acid as eluent. There was thus obtained the required starting material (0.112 g); NMR Spectrum: (CDCl$_3$) 1 46 (s, 6H), 3.03 (s, 2H), 3.44 (s, 2H), 3.9 (s, 311), 3.95 (s, 3H), 5.02 (m, 2H), 5.83 (m, 1H).

EXAMPLE 5

A mixture of 3-(2-methylamino-3,5-dimethyl-1,4-benzoquinonyl)-3-methylbutyric acid (crude, 3.73 g), 4-[bis(2-chloroethyl)amino]phenol hydrochloride (3.96 g), 2-(1-benzotriazolyl)-1,1,3,3-tetramethyluronium hexafluorophosphate(V) (5.55 g), triethylamine (4.22 g) and acetonitrile (115 ml) was stirred at ambient temperature for 22 hours. The mixture was evaporated and the residue was purified by column chromatography on silica using a 4:1 mixture of hexane and ethyl acetate as eluent. There was thus obtained 4-[bis(2-chloroethyl)amino]phenyl 3-(2-methylamino-3,5-dimethyl-1,4-benzoquinonyl)-3-methylbutyrate as a gum (1.95 g); NMR Spectrum: (CDCl$_3$) 1.5 (s, 6H), 2.0 (s, 3H), 2.2 (s, 3H), 3.05 (d, 3H), 3.15 (s, 2H), 3.55–3.7 (m, 8H), 5.15 (broad s, 1H), 6.6 (d, 2H), 6.9 (d,2H); Mass Spectrum: (M+H$^+$) 484, 482, 480.

The 3-(2-methylamino-3,5-dimethyl-1,4-benzoquinonyl)-3-methylbutyric acid used as a starting material was obtained as follows:

An ethanolic solution of methylamine (8.03M, 40 ml) was added to a stirred solution of 3-(2-bromo-3,5-dimethyl-1,4-benzoquinonyl)-3-methylbutyric acid (*J. Org. Chem.*, 1989, 54, 3303–3310; 10.03 g) in methanol (400 ml) and the resultant mixture was stirred at ambient temperature in the dark for 18 hours. The mixture was poured into water (3 L) and acidified to pH2 by the addition of 5N aqueous hydrochloric acid. The mixture was extracted with diethyl ether. The organic phase was washed with a saturated aqueous sodium chloride solution, dried (MgSO$_4$) and evaporated. There was thus obtained a crude sample of the required starting material as a gum (6.14 g); Mass Spectrum: (M–H$^-$) 264.

EXAMPLE 6

A mixture of 1-(3-dimethylaminopropyl)-3-ethylcarbodiimide hydrochloride (0.271 g) in methylene chloride (3 ml) was added to a stirred mixture of 3-[3,5-dimethyl-2-(2-morpholinoethylamino)-1,4-benzoquinonyl]-3-methylbutyric acid (crude, 0.413 g), 4-[bis(2-chloroethyl)amino]phenol hydrochloride (0.322 g), 4-dimethylaminopyridine (0.327 g) and methylene chloride (12 ml). The resultant mixture was stirred at ambient temperature for 4 hours. The mixture was evaporated and the residue was purified by column chromatography on silica using increasingly polar mixtures of hexane and ethyl acetate as eluent. There was thus obtained 4-[bis(2-chloroethyl)amino]phenyl 3-[3,5-dimethyl-2-(2-morpholinoethylamino)-1,4-benzoquinonyl]-3-methylbutyrate as a gum (0.061 g); NMR Spectrum: (CDCl$_3$) 1.5 (s, 6H), 1.95 (s, 3H), 2.2 (s, 3H), 2.4 (t, 4H), 2.55 (t, 2H), 3.15 (s, 2H), 3.45 (m, 2H), 3.7 (m, 12H), 5.65 (t, 1H), 6.6 (d, 2H), 6.85 (d, 2H); Mass Spectrum: (M+H$^+$) 583, 581, 579.

The 3-[3,5-dimethyl-2-(2-morpholinoethylamino 1,4-benzoquinonyl]-3-methylbutyric acid used as a starting material was obtained as follows:

A mixture of 3-(2-bromo-3,5-dimethyl-1,4-benzoquinonyl)-3-methylbutyric acid (1.14 g), 2-morpholinoethylamine (2.35 g) and DMA (10 ml) was stirred for 20 hours in the dark. The mixture was evaporated and the residue was partitioned between ethyl acetate and an aqueous sodium chloride solution. The aqueous solution was acidified to pH2 by the addition of dilute aqueous hydrochloric acid and the resultant solution was passed down a HP20 resin column (a cross-linked styrene divinylbenzene resin from Biotage UK Ltd., Hertford, UK) using initially water and then acetonitrile as eluent. There was thus obtained a crude sample of the required starting material as a gum (0.436 g); Mass Spectrum: (M–H$^-$) 363.

EXAMPLE 7

Using an analogous procedure to that described in Example 5, 3-[2-(2-acetamidoethylamino)-3-methoxy-5-methyl-1,4-benzoquinonyl]-3-methylbutyric acid was reacted with 4-[bis(2-chloroethyl)amino]phenol to give a product which was further purified by reversed-phase HPLC using a 39:11 mixture of methanol and water as eluent. There was thus obtained 4-[bis(2-chloroethyl)amino]phenyl 3-[2-(2-acetamidoethylamino)-3-methoxy-5-methyl-1,4-benzoquinonyl]-3-methylbutyrate as a gum in 13% yield; NMR Spectrum: (CDCl$_3$) 1.55 (s, 6H), 1.85 (s, 3H), 2.2 (s, 3H), 3.2 (s, 2H), 3.5–3.8 (m, 13H), 5.95 (broad s, 1H), 6.6 (d, 2H), 6.85 (d, 2H); Mass Spectrum (M+H$^+$) 571, 569, 567.

The 3-[2-(2-acetamidoethylamino)-3-methoxy-5-methyl-1,4-benzoquinonyl]-3-methylbutyric acid used as a starting material was obtained as follows A mixture of 3-(2,3-dimethoxy-5-methyl-1,4-benzoquinonyl)-3-methylbutyric acid (*J. Orz. Chem.*, 1989, 54, 3303–3310; 1.2 g), N-acetylethylenediamine (1.43 g) and methanol (20 ml) was stirred at ambient temperature for 20 days in the dark. The mixture was evaporated and the residue was dissolved in dilute aqueous hydrochloric acid and purified by chromatography on a HP20 resin column using initially water and then a 4:1 mixture of water and acetonitrile as eluent. There was thus obtained a crude sample of the required starting material as a gum (1.19 g); Mass Spectrum: (M–H$^-$) 351.

EXAMPLE 8

Using an analogous procedure to that described in Example 5, 3-(3-allyl-2,5-dimethyl-1,4-benzoquinonyl)-3-methylbutyric acid was reacted with 4-[bis(2-chloroethyl)

amino]phenol to give 4-[bis(2-chloroethyl)amino]phenyl 3-(3-allyl-2,5-dimethyl-1,4-benzoquinonyl)-3-methylbutyrate as an oil in 26% yield; NMR Spectrum: (CDCl$_3$) 1.52 (s, 6H), 1.96 (s, 3H), 2.17 (s, 3H), 3.15 (d, 2H), 3.2 (s, 2H), 3.56–3.72 (m, 8H), 4.99 (m, 2H), 5.72 (m, 1H), 6.58–6.88 (m, 4H); Mass Spectrum: (M+H$^+$) 496,494,492.

The 3-(3-allyl-2,5-dimethyl-1,4-benzoquinonyl)-3-methylbutyric acid used as a starting material was obtained as follows:

Allyl bromide (8.45 g) was added to a mixture of 6-hydroxy-4,4,5,8-tetramethyl-3,4-dihydrocoumarin (*J. Org. Chem.*, 1989, 54, 3303–3310; 5 g), potassium carbonate (9.4 g) and DMF (50 ml). The resultant mixture was stirred at ambient temperature for 2 hours. The mixture was partitioned between diethyl ether and water. The organic phase was washed with water and with a saturated aqueous sodium chloride solution, dried (MgSO$_4$) and evaporated. There was thus obtained 6-allyloxy-4,4,5,8-tetramethyl-3,4-dihydrocoumarin (5.2 g); NMR Spectrum: (CDCl$_3$) 1.48 (s, 6H), 2.28 (s, 3H), 2.34 (s, 3H), 2.57 (s, 2H), 4.5 (m, 2H), 5.36 (m, 2H), 6.07 (m, 1H), 6.63 (s, 1H).

A mixture of a portion (3 g) of the material so obtained and N,N-diethylaniline (40 ml) was stirred and heated to 180° C. for 18 hours. The mixture was cooled to ambient temperature, acidified by the addition of 5N aqueous hydrochloric acid and extracted with ethyl acetate. The organic phase was washed with water and with a saturated aqueous sodium chloride solution, dried (MgSO$_4$) and evaporated. There was thus obtained 7-allyl-6-hydroxy-4,4,5,8-tetramethyl-3,4-dihydrocoumarin (2.9 g); NMR Spectrum: (CDCl$_3$) 1.48 (s, 6H), 2.24 (s, 3H), 2.37 (s, 3H), 2.58 (s, 2H), 3.44 (d, 2H), 4.84 (broad s, 1H), 5.12 (m, 2H), 5.98 (m, 1H).

A mixture of a portion (2.6 g) of the material so obtained, 1N aqueous sodium hydroxide solution (17.5 ml) and acetonitrile (50 ml) was stirred at ambient temperature in air for 4 days. The mixture was acidified by the addition of 2N aqueous hydrochloric acid and extracted with ethyl acetate. The organic phase was washed with a saturated aqueous sodium chloride solution, dried (MgSO$_4$) and evaporated. There was thus obtained 3-( 3-allyl-2,5-dimethyl-1,4-benzoquinonyl)-3-methylbutyric acid as an oil (2.7 g); NMR Spectrum: (CDCl$_3$) 1.44 (s, 6H), 1.95 (s, 3H), 2.14 (s, 3H), 3.0 (s, 2H), 3.19 (d, 2H), 5.0 (m, 2H), 5.77 (m, 1H).

EXAMPLE 9

Using an analogous procedure to that described in Example 5, 3-(2,5-dimethyl-3-propyl-1,4-benzoquinonyl)-3-methylbutyric acid was reacted with 4-[bis(2-chloroethyl) amino]phenol to give 4-[bis(2-chloroethyl)amino]phenyl 3-(2,5-dimethyl-3-propyl-1,4-benzoquinonyl)-3-methylbutyrate in 32% yield; NMR Spectrum: (CDCl$_3$) 0.91 (t, 3H), 1.39 (m, 2H), 1.52 (s, 6H), 1.95 (s, 3H), 2.18 (s, 3H), 2.35 (t, 2H), 3.2 (s, 2H), 3.55–3.73 (m, 8H), 6.6 (d, 2H), 6.84 (d, 2H); Mass Spectrum: (M+H$^+$) 498, 496, 494.

The 3-(2,5-dimethyl-3-propyl-1,4-benzoquinonyl)-3-methylbutyric acid used as a starting material was obtained as follows:

A mixture of 7-allyl-6-hydroxy-4,4,5,8-tetramethyl-3,4-dihydrocoumarin (3 g), 10% palladium-on-charcoal catalyst (0.5 g) and methanol (75 ml) was stirred under an atmosphere of hydrogen for one hour. The mixture was filtered and the filtrate was evaporated. There was thus obtained 6-hydroxy-4,4,5,8-tetramethyl-7-propyl-3,4-dihydrocoumarin (1.06 g); NMR Spectrum: (CDCl$_3$) 1.03 (t, 3H), 1.46 (s, 6H), 1.57 (s, 2H), 2.23 (s, 3H), 2.36 (s, 3H), 2.6 (m, 4H), 4.58 (s, 1H).

A mixture of the material so obtained, 1N aqueous sodium hydroxide solution (4.5 ml) and acetonitrile (15 ml) was stirred at ambient temperature in air for 4 days. The mixture was acidified by the addition of 2N aqueous hydrochloric acid and extracted with ethyl acetate. The organic phase was washed with a saturated aqueous sodium chloride solution, dried (MgSO$_4$) and evaporated. There was thus obtained 3-(2,5dimethyl-3-propyl-1,4-benzoquinonyl)-3-methylbutyric acid as an oil (1.12 g); NMR Spectrum: (CDCl$_3$) 0.93 (t, 3H), 1.38–1.5 (m, 8H), 1.95 (s, 3H), 2.14 (s, 3H), 2.39 (m, 2H), 3.0 (s, 2H).

EXAMPLE 10

N,N'-dicyclohexylcarbodiimide (0.33 g) was added to a stirred mixture of 3-(2,3-dimethoxy-5-methyl-1,4-benzoquinonyl)-3-methylbutyric acid (0.45 g), N-hydroxybenzotriazole (0.01 g) and methylene chloride (20 ml) which had been cooled in an ice-bath and the resultant mixture was stirred for 5 minutes. A solution of 4-[bis(2-chloroethyl)amino]phenol hydrochloride (0.43 g) and triethylamine (0.45 ml) in methylene chloride (5 ml) was added and the reaction mixture was stirred at ambient temperature for 1.5 hours. The mixture was evaporated and the residue was purified by column chromatography on silica using increasingly polar mixtures of hexane and ethyl acetate as eluent. The material so obtained was purified further by reversed-phase column chromatography on silica using decreasingly polar mixtures of water and methanol as eluent. There was thus obtained 4-[bis(2-chloroethyl)amino] phenyl 3-(2,3-dimethoxy-5-methyl-1,4-benzoquinonyl)-3-methylbutyrate as an oil (0.19 g); NMR Spectrum: (CDCl$_3$) 1.52 (s, 6H), 2.18 (s, 3H), 3.23 (s, 2H), 3.57–3.76 (m, 8H), 3.89 (s, 3H), 3.95 (s, 3H), 6.62 (d, 2H), 6.87 (d, 2H); Mass Spectrum: (M+H$^+$) 498.

EXAMPLE 11

Using an analogous procedure to that described in Example 5,3-(2,3,5-trimethyl-1,4-benzoquinonyl)-3-methylbutric acid was reacted with 4-[bis(2-chloroethyl) amino]phenol to give 4-[bis(2-chloroethyl)amino]phenyl 3-(2,3,5-trimethyl-1,4-benzoquinonyl)-3-methylbutyrate as a solid in 40% yield; NMR Spectrum: (CDCl$_3$) 1.52 (s, 6H), 1.9 (s, 3H), 1.92 (s, 3H), 2.18 (s, 3H), 3.2 (s, 2H), 3.55–3.72 (m, 8H), 6.6–6.9 (m, 4H); Mass Spectrtun: (M+H$^+$) 466.

The 3-(2,3,5-trimethyl-1,4-benzoquinonyl)-3-methylbutyric acid used as a starting material was obtained as follows:

Methyl 3,3-dimethylacrylate (6 g) was added to a stirred mixture of 2,3,5-trimethylhydroquinone (7.6 g) and methanesulphonic acid (40 ml) which had been heated to 75° C. and the mixture was stirred at 75° C. for 1 hour. The mixture was poured onto a mixture of ice and water and the resultant mixture was extracted with ethyl acetate. The organic phase was washed with a 5% aqueous sodium bicarbonate solution, dried (MgSO$_4$) and evaporated. There was thus obtained 6-hydroxy-4,4,5,7,8-pentamethyl- 3,4-dihydrocoumarin (10.7 g); NMR Spectrum: (CDCl$_3$) 1.48 (s, 6H), 2.18 (s, 3H), 2.22 (s, 3H), 2.37 (s, 3H), 2.55 (s, 2H), 4.6 (s, 1H).

A mixture of a portion (5.85 g) of the material so obtained, 0.5N aqueous sodium hydroxide solution (50 ml) and acetonitrile (100 ml) was stirred at ambient temperature in air for 18 hours. The mixture was acidified by the addition of 5N aqueous hydrochloric acid and extracted with ethyl acetate. The organic phase was washed with water and with a saturated aqueous sodium chloride solution, dried (MgSO$_4$)

and evaporated. There was thus obtained the required starting material (4.1 g) which was used without fuirther purification; NMR Srectrum: (CDCl₃) 1 46 (s, 6H), 1.93 (s, 3H), 1.96 (s, 3H), 2.15 (s, 3H), 3.02 (s, 2H).

EXAMPLE 12

Using an analogous procedure to that described in Example 5, 3-(2,5-dimethyl-1,4-benzoquinonyl)-3-methylbutyric acid was reacted with 4-[bis(2-chloroethyl)amino]phenol to give 4-[bis(2-chloroethyl)amino]phenyl 3-(2,5-dimethyl-1,4-benzoquinonyl)-3-methylbutyrate as a solid in 9% yield; NMR Spectrun: (CDCl₃) 1.52 (s, 6H), 1.98 (m, 3H), 2.16 (s, 3H), 3.2 (s, 2H), 3.55–3.73 (m, 8H), 6.42 (m, 1 H), 6.6–6.9 (m, 4H); Mass Spectrum: (M+H⁺) 452.

The 3-(2,5-dimethyl-1,4-benzoquinonyl)-3-methylbutyric acid used as a starting material was obtained as follows:

A mixture of 6-hydroxy-4,4,5,8-tetramethyl-3,4-dihydrocoumarin (J. Org. Chem. 1989, 54, 3303–3310; 2.2 g), 1N aqueous sodium hydroxide solution (10 ml) and acetonitrile (20 ml) was stirred at ambient temperature in air for 2 days. The mixture was acidified by the addition of 5N aqueous hydrochloric acid and extracted with ethyl acetate. The organic phase was washed with water and with a saturated aqueous sodium chloride solution, dried (MgSO₄) and evaporated. There was thus obtained the required starting material (1.8 g) which was used without fuirther purification; NMR Spectrum: (CDCl₃) 1 44 (s, 6H), 2.12 (s, 3H), 2.4 (s, 3H), 3.02 (d, 2H), 7.25 (s, 1H).

EXAMPLE 13

Using an analogous procedure to that described in Example 1,3-(5-isopropylamino-2-methyl-1,4-benzoquinon-3-yl)-3-methylbutyric acid was reacted with 4-[bis(2-chloroethyl)amino]phenol and the product was purified by reversed-phase column chromatography on silica using decreasingly polar mixtures of water and methanol as eluent. There was thus obtained 4-[bis(2-chloroethyl)amino] phenyl 3-(5-isopropylamino-2-methyl-1,4-benzoquinon-3-yl)-3-methylbutyrate as a gum in 6% yield; NMR Spectrum: (CDCl₃) 1.2 (d, 6H), 1.55 (s, 6H), 2.22 (s, 3H), 3.15 (s, 2H), 3.45 )m, 1H), 3.5–3.75 (m, 8H), 5.35 (d, 1H), 5.4 (s, 1H), 6.6 (d, 2H), 6.85 (d, 2H); Mass Spectrum: (M+H⁺) 495.

The 3-(5-isopropylamino-2-metbyl-1,4-benzoquinon-3-yl)-3-methylbutyric acid used as a starting material was obtained as follows:

A mixture of 6-hydroxy-4,4,5,8-tetramethyl-3,4-dihydrocoumarin (17.5 g), N-bromosuccinimide (15.2 g) and chloroform (2.5 L) was stirred at ambient temperature for 2.5 hours. The mixture was evaporated and the residue was purified by column chromatography on silica using a 5:1 mixture of hexane and ethyl acetate as eluent. There was thus obtained 7-bromo-6-hydroxy-4,4,5,8-tetramethyl-3,4-dihydrocoumarin (6 g); NMR Spectrum: (CDCl₃) 1.45 (s, 6H), 2.39 (s, 3H), 2.45 (s, 3H), 2.6 (s, 2H), 5.6 (s, 1H).

A mixture of the material so obtained, pyridinium chlorochromate (34 g) and DMA (150 ml) was stirred at ambient temperature for 5 hours. The mixture was evaporated and the residue was partitioned between ethyl acetate and water. The organic phase was dried (MgSO₄) and evaporated. There was thus obtained 3-(3-bromo-2,5-dimethyl-1,4-benzoquinonyl)-3-methylbutyric acid as an oil (5.3 g); NMR Spectrum: (CDCl₃) 1.4 (s, 6H), 2.15 (s, 3H), 2.2 (s, 3H), 3.0 (s, 2H).

A mixture of a portion (3.9 g) of the material so obtained, isopropylamine (15 ml) and methanol (150 ml) was stirred at ambient temperature for 2 days. The mixture was evaporated and the residue was partitioned between diethyl ether and a saturated aqueous sodium chloride solution. The organic phase was dried (MgSO₄) and evaporated. There was thus obtained the required starting material as a gum (2.25 g); Mass Spectrum: (M+H⁺) 280.

EXAMPLE 14

4-[Bis(2-chloroethyl)amino]phenol hydrochloride (0.537 g) was added to a stirred mixture of 3-[3-methoxy-5-methyl-2-(2-morpholinoethylamino)-1,4-benzoquinonyl]-3-methylbutyric acid (0.7 g), 1-(3-dimethylaminopropyl)-3-ethylcarbodiimide hydrochloride (0.42 g), N-hydroxybenzotriazole (0.295 g), N-methylmorpholine (1.09 ml) and methylene chloride (70 ml) which had been cooled in an ice-bath. The resultant mixture was stirred at ambient temperature for 20 hours. The mixture was evaporated and the residue was purified by column chromatography on silica using increasingly polar mixtures of hexane and ethyl acetate as eluent. There was thus obtained 4-[bis(2-chloroethyl)amino]phenyl 3-[3-dimethoxy-5-methyl-2-(2-morpholinoethylamino)-1,4-benzoquinonyl]-3-methylbutyrate as a gum (0.246 g); NMR Spectrum: (CDCl₃) 1.5 (s, 6H), 2.1 (s, 3H), 2.55 (t, 2H), 3.18 (s, 2H), 3.5–3.7 (m, 4H), 3.75 (s, 3H), 5.65 (t, 1H), 6.6 (d, 2H), 6.85 (d, 2H); Mass Spectrum: (M+H⁺) 596.

The 3-[3-methoxy-5-methyl-2-(2-morpholinoethylamino)-1,4-benzoquinonyl]-3-methylbutyric acid used as a starting material was obtained as follows:

A mixture of 3-(2,3-dimethoxy-5-methyl-1,4-benzoquinonyl)-3-methylbutyric acid (0.524 g), 2-morpholinoethylamine (1.21 g) and methanol (25 ml) was stirred at ambient temperature in the dark for 10 hours. The mixture was evaporated and the residue was dissolved in dilute aqueous hydrochloric acid (10 ml). The solution was applied to a HP20 resin column and eluted initially with water and then with a 4:1 mixture of water and acetonitrile. There was thus obtained a crude sample of the required starting material as a gum (0.462 g); Mass Spectrum: (M−H⁻) 379.

EXAMPLE 15

Using an analogous procedure to that described in Example 5, 3-[2-(2-tert-butoxycarbonylethylamino)-3-methoxy-5-methyl-1,4-benzoquinonyl]-3-methylbutyric acid was reacted with 4-[bis(2-chloroethyl)amino]phenol. The mixture was evaporated and the residue was purified by column chromatography on silica using increasingly polar mixtures of hexane and ethyl acetate as eluent. The product so obtained was further purified by reversed-phase column chromatography on silica using decreasingly polar mixtures of water and methanol as eluent. There was thus obtained 4-[bis(2-chloroethyl)amino]phenyl 3-[2-(2-tert-butoxycarbonylethylamino)-3-methoxy-5-methyl-1,4-benzoquinonyl]-3-methylbutyrate as a gum in 1.5% yield; NMR Spectrum: (CDCl₃) 1.45 (s, 9H), 1.5 (s, 6H), 2.2 (s, 31), 2.45 (s, 3H), 3.15 (s, 2H), 3.6 (m, 4H), 3.7 (m, 6H), 3.75 (2, 3H), 5.4 (t, 1H), 6.6 (d, 2H), 6.85 (d, 2H); Mass Spectrum: (M+H⁺) 613.

The 3-[2-(2-tert-butoxycarbonylethylamino)-3-methoxy-5-methyl-1,4-benzoquinonyl]-3-methylbutyric acid used as a starting material was obtained as follows:

A mixture of 3-(2,3-dimethoxy-5-methyl-1,4-benzoquinonyl)-3-methylbutyric acid (1.23 g), 2-(tert-butoxycarbonyl)ethylamine hydrochloride (2.38 g), triethylamine (1.76 g) and methanol (25 ml) was stirred at ambient temperature in the dark for 20 days. The mixture was evaporated and the residue was partitioned between diethyl ether and a dilute aqueous hydrochloric acid solution. The organic phase was dried (MgSO$_4$) and evaporated. There was thus obtained the required starting material as a gum (1.26 g); Mass S1ectrum: (M+H$^+$) 396.

EXAMPLE 16

Using an analogous procedure to that described in Example 1,3-(2-pyrrolidin-1-yl-1,4-benzoquinon-6-yl)-3-methylbutyric acid was reacted with 4-[bis(2-chloroethyl) amino]phenol and the product was purified by column chromatography on silica using a 1:1 mixture of petroleum ether (b.p. 40 to 60° C.) and ethyl acetate as eluent. There was thus obtained 4-[bis(2-chloroethyl)amino]phenyl 3-(2-pyrrolidin-1-yl-1,4-benzoquinonyl)-3-methylbutyrate in 60% yield; NMR Spectrum: (CDCl$_3$) 1.42 (s, 6H), 1.9 (m, 4H), 3.04 (s, 2H), 3.0–3.8 (broad m, 4H), 3.57 (t, 4H), 3.68 (t, 4H), 5.4 (s, 1H), 6.48 (s, 1H), 6.6 (d, 2H), 6.81 (d, 2H); Mass Spectrum: (M+H$^+$) 493, 495 & 497.

The 3-(2-pyrrolidin-1-yl-1,4-benzoquinon-6-yl)-3-methylbutyric acid used as a starting material was obtained as follows:

A solution of sodium periodate (1 g) in water (1 ml) was added to a stirred solution of 3-(1,4-benzoquinonyl)-3-methylbutyric acid (1 g) in chloroform (30 ml). Pyrrolidine (0.8 ml) was added dropwise and the resultant mixture was stirred at ambient temperature for 1 hour. The reaction mixture was dried (MgSO$_4$) and evaporated and the residue was purified by reversed-phase HPLC using decreasingly polar mixtures of water, methanol and acetic acid as eluent. There was thus obtained the required starting material (0.52 g); NMR Spectrum: (CDCl$_3$) 1.33 (s, 6H), 1.95 (m, 4H), 2.86 (s, 2H), 3.1–3.9 (broad s, 4H), 5.42 (d, 1H), 6.45 (d, 1H).

EXAMPLE 17

Using an analogous procedure to that described in Example 10 except that the reaction mixture was heated to reflux for 3 hours rather than being stirred at ambient temperature for 1.5 hours, 3-methyl-3-(3,5-dimethyl-1,4-benzoquinonyl)butyric acid was reacted with 4-[bis(2-chloroethyl)amino]phenol and the product was purified by column rang chromatography on silica using a 9:1 mixture of hexane and ethyl acetate as eluent. There was thus obtained 4-[bis(2-chloroethyl)amino]phenyl 3-methyl-3-(3,5-dimethyl-1,4-benzoquinonyl)butyrate in 8% yield; NMR Spectrum: (CDCl$_3$) 1.5 (s, 6H), 1.95 (s, 3H), 2.2 (s, 3H), 3.24 (s, 2H), 3.54–3.75 (m, 8H), 6.46 (m, 1H), 6.62 (d, 2H), 6.87 (m, 2H); Mass Spectrum: (M+H$^+$) 452.

EXAMPLE 18

Using an analogous procedure to that described in Example 1, 3-(5-methyl-3-propyl-1,4-benzoquinon-2-yl)-3-methylbutyric acid was reacted with 4-[bis(2-chloroethyl) amino]phenol and the product was purified by column chromatography on silica using a 4:1 mixture of petroleum ether (b.p. 40 to 60° C.) and ethyl acetate as eluent. There was thus obtained 4-[bis(2-chloroethyl)amino]phenyl 3-(5-methyl-3-propyl-1,4-benzoquinon-2-yl)-3-methylbutyrate in 53% yield; NMR Spectrum: (CDCl$_3$) 1.0 (t, 3H), 1.44 (m, 2H4), 1.54 (s, 6H), 1.94 (s, 3H), 2.61 (m, 2H), 3.23 (s, 2H), 3.59 (t, 4H), 3.68 (t, 4H), 6.46 (s, 1H), 6.61 (d, 2H), 6.86 (d, 2H); Mass Spectrum: (M+H$^+$) 502, 504 & 506.

The 3-(5-methyl-3-propyl-1,4-benzoquinon-2-yl)-3-methylbutyric acid used as a starting material was obtained as follows:

A mixture of 6-hydroxy-4,4,7-trimethyl-3,4-dihydrocoumarin (*J. Amer. Chem. Soc.*, 1983, 105, 2752–2760; 10 g), allyl bromide (12.6 ml), potassium carbonate (20 g) and DMF (100 ml) was stirred at ambient temperature for 2 hours. The mixture was partitioned between diethyl ether and water. The organic phase was washed with a saturated aqueous chloride solution, dried (MgSO$_4$) and evaporated. There was thus obtained 6-allyloxy-4,4,7-trimethyl-3,4-dihydrocoumarin (12 g); NMR Spectrum: (CDCl$_3$) 1.32 (s, 6H), 2.22 (s, 3H), 2.58 (s, 2H), 4.53 (m, 2H), 5.35 (m, 2H), 6.05 (m, 2H), 6.71 (s, 1H), 6.85 (s, 1H).

A mixture of a portion (6 g) of the material so obtained and N,N-dimethylaniline (96 ml) was stirred and heated to 200° C. for 5 hours. The mixture was evaporated and the residue was purified by column chromatography on silica using a 4:1 mixture of petroleum ether (b.p. 40 to 60° C.) and ethyl acetate as eluent. There was thus obtained 5-allyl-6-hydroxy-4,4,7-trimethyl-3,4-dihydrocoumarin (3.7 g); NMR Spectrum: (CDCl$_3$) 1.42 (s, 6H), 2.22 (s, 3H), 2.56 (s, 2H), 3.58 (m, 2H), 4.87 (s, 1H), 5.2 (m, 2H), 6.08 (m, 1H), 6.8 (s, 1H).

A mixture of a portion (1 g) of the material so obtained, 10% palladium-on-charcoal catalyst (0.15 g) and ethanol (60 ml) was stirred under 3 atmospheres pressure of hydrogen for 30 minutes. The mixture was filtered and the filtrate was evaporated to give 6-hydroxy-5-propyl-4,4,7-trimethyl-3,4-dihydrocoumarin (1 g); NMR Spectrum: (CDCl$_3$) 1.06 (t, 3H), 1.46 (s, 6H), 1.66 (m, 2H), 2.21 (s, 3H), 2.56 (s, 2H), 2.72 (m, 2H), 4.57 (s, 1H), 6.72 (s, 1H).

A solution of the material so obtained in acetonitrile (12 ml) was stirred and heated to reflux. A solution of ferric chloride hexahydrate (2.18 g) in a mixture of acetonitrile (10 ml) and water (10 ml) was added portionwise during 2 hours. The mixture was cooled to ambient temperature and partitioned between diethyl ether and a 5% aqueous sodium bicarbonate solution. The aqueous phase was acidified by the addition of 2N aqueous hydrochloric acid and extracted with diethyl ether. The resultant organic phase was dried (MgSO$_4$) and evaporated. There was thus obtained 3-(5-methyl-3-propyl-1,4-benzoquinon-2-yl)-3-methylbutyric acid as an oil (0.335 g); NMR Spectrum: (CDCl$_3$) 0.99 (t, 3H), 1.42 (m, 2H), 1.46 (s, 6H), 1.97 (s, 3H), 2.6 (m, 2H), 3.03 (s, 2H), 6.45 (s, 1H).

EXAMPLE 19

Using an analogous procedure to that described in Example 1, 3-[3-(2-ethoxycarbonylethyl)-5-methyl-1,4-benzoquinon-2-yl]-3-methylbutyric acid was reacted with 4-[bis(2-chloroethyl)amino]phenol and the product was purified by column chromatography on silica using a 4:1 mixture of petroleum ether (b.p. 40 to 60° C.) and ethyl acetate as eluent. There was thus obtained 4-[bis(2-chloroethyl)amino]phenyl 3-[3-(2-ethoxycarbonylethyl)-5-methyl-1,4-benzoquinon-2-yl]-3-methylbutyrate in 60% yield; NMR Soectrum: (CDCl$_3$) 1.26 (t, 3H), 1.54 (s, 3H), 1.55 (s, 3H), 1.94 (s, 3H), 2.46 (m, 2H), 2.96 (m, 2H), 3.25 (s, 2H), 3.59 (t, 4H), 3.68 (t, 4H), 4.15 (m, 2H), 6.48 (s, 1H), 6.61 (d, 2H), 6.86 (d, 2H); Mass Spectnum: (M+Na$^+$) 560 & 562.

The 3-[3-(2-ethoxycarbonylethyl)-5-methyl-1,4-benzoquinon-2-yl]-3-methylbutyric acid used as a starting material was obtained as follows:

A mixture of 6-hydroxy-4,4,7-trimethyl-3,4-dihydrocoumarin (*J. Amer. Chem. Soc.*, 1983, 105, 2752–2760; 6.7 g), hexamethylenetetramine (4.56 g) and trifluoroacetic acid (70 ml) was stirred and heated to 60° C. for 16 hours. Water (50 ml) was added and the mixture was stirred at ambient temperature for 3 hours. The mixture was evaporated and the residue was purified by column chromatography on silica using a 5:1 mixture of petroleum ether (b.p. 40 to 60° C.) and ethyl acetate as eluent. There was thus obtained 5-formyl-6hydroxy-4,4,7-trimethyl-3,4-dihydrocoumarin (6 g, 80%); NMR Spectnim: ($CDCl_3$) 1.71 (s, 6H), 2.38 (s, 3H), 2.74 (s, 2H), 7.24 (s, 1H), 10.63 (s, 1H).

A mixture of a portion (5 g) of the material so obtained, benzyl-bromide (3 ml), potassium carbonate (3.25 g) and DMF (100 ml) was stirred and heated to 80° C. for 1 hour. The mixture was poured in water (200 ml) and extracted with diethyl ether. The organic extract was washed with a saturated aqueous solution of sodium chloride, dried ($MgSO_4$) and evaporated to give 6-benzyloxy-5-formyl-4,4,7-trimethyl-3,4-dihydrocoumarin (6.9 g); NMR Spectrum: ($CDCl_3$) 1.38 (s, 6H); 2.32 (s, 3H); 2.55 (s, 2H); 4.83 (s, 2H); 7.05 (s, 1H); 7.39 (m, 5H); 10.53 (s, 1H).

A mixture of 6-benzyloxy-5-formyl-4,4,7-trimethyl-3,4-dihydrocoumarin (7.4 g), (ethoxycarbonylmethylene)triphenylphosphorane (8 g) and toluene (100 ml) was stirred and heated to reflux for 16 hours. The resultant mixture was cooled to ambient temperature and poured into a 5% aqueous sodium bicarbonate solution. The mixture was extracted with ethyl acetate and the extract was washed with a saturated aqueous sodium chloride solution. dried ($MgSO_4$) and evaporated. The residue was purified by column chromatography on silica using a 3:2 mixture of petroleum ether (b.p. 40 to 60° C.) and diethyl ether as eluent. There was thus obtained ethyl 3-(6-benzyloxy-4,4,7-trimethyl-3,4-dihydrocournarin-5-yl)acrylate as a white solid (7.9 g); NMR Spectrum: ($CDCl_3$) 1.3 (t, 3H), 1.41 (s, 6H), 2.31 (s, 3H), 2.56 (s, 2H), 2.23 (m, 2H), 2.63 (s, 2H), 6.26 (d, 1H), 7.9 (s, 1H), 7.35 (m, 5H), 7.82 (d, 1H).

A mixture of the material so obtained, 10% palladium-on-carbon catalyst (1 g) and ethanol (500 ml) was stirred under an atmosphere pressure of hydrogen for 1.5 hours. The catalyst was removed by filtration and the solvent was evaporated to give ethyl 3-(6-benzyloxy-4,4,7-trimethyl-3,4-dihydrocoumarin-5-yl)propionate as a white solid (6.1 g); NMR Spectrum: ($CDCl_3$) 1.29 (t, 3H), 1.46 (s, 6H), 2.22 (s, 3H), 2.56 (s, 2H), 2.74 (t, 2H), 3.13 (t, 2H), 4.2 (m, 2H), 6.78 (s, 1H), 6.81 (s, 1H).

A solution of ferric chloride hexahydrate (21 g) in a mixture of acetonitrile (50 ml) and water (50 ml) was added in small portions during 45 minutes to a stirred solution of a portion (5 g) of the ethyl propionate so obtained in acetonitrile (50 ml). The resultant mixture was heated to 90° C. for 45 minutes. The mixture was cooled to ambient temperature and partitioned between diethyl ether and a 5% aqueous sodium bicarbonate solution. The aqueous phase was acidified to pH 2 by the addition of 2N aqueous hydrochloric acid and extracted with diethyl ether. The resultant organic phase was dried ($MgSO_4$) and evaporated. The residue was purified by column chromatography on silica using a 50:50:0.1 mixture of petroleum ether (b.p. 40 to 60° C.), diethyl ether and acetic acid as eluent. There was thus obtained 3-[3-(2-ethoxycarbonylethyl)-5-methyl-1,4-benzoquinon-2-yl]-3-methylbutyric acid (0.48 g); NMR Spectrum: ($CDCl_3$) 1.26 (t, 3H), 1.47 (s, 6H), 1.98 (s, 3H), 2.45 (m, 2H), 2.97 (m, 2H), 3.06 (s, 2H), 4.15 (m, 2H), 6.48 (s, 1H).

EXAMPLE 20

Using an analogous procedure to that described in Example 1, 3-[2-(2-methoxycarbonylethyl)-3,5-dimethyl-1,4-benzoquinonyl]-3-methylbutyric acid was reacted with 4-[bis(2-chloroethyl)amino]phenol and the product was purified by column chromatography on silica using a 6:1 mixture of petroleum ether (b.p. 40 to 60° C.) and ethyl acetate as eluent. The product so obtained was further purified by reversed-phase column chromatography on silica using an 80:20:1 mixture of methanol, water and acetic acid as eluent. There was thus obtained 4-[bis(2-chloroethyl)amino]phenyl 3-[2-(2-methoxycarbonylethyl)-3,5-dimethyl-1,4-benzoquinonyl]-3-methylbutyrate in 21% yield; NMR Spectrum: ($CDCl_3$) 1.5 (s, 6H), 1.97 (s, 3H), 2.16 (s, 3H), 2.4 (m, 1H), 2.72 (m, 1H), 3.2 (s, 2H), 3.58 (m, 4H), 3.65 (s, 3H), 3.67 (m, 4H), 6.61 (d, 2H), 6.86 (d, 2H); Mass Spectrum: ($M+Na^+$) 560, 562 & 564.

The 3-[2-(2-methoxycarbonylethyl)-3,5-dimethyl-1,4-benzoquinonyl]-3-methylbutyric acid used as a starting material was obtained as follows:

A mixture of tert-butyl 3-methyl-3-(3,5-dimethyl-1,4-benzoquinonyl)butyrate (0.5 g), succinic acid momomethyl ester (0.45 g) and silver nitrate (0.085 g) was dissolved in a mixture of acetonitrile (6.5 ml) and water (6.5 ml). The mixture was stirred and heated to 75° C. and a solution of sodium persulphate ($Na_2S_2O_8$; 0.265 g) in water (2 ml) was added dropwise over a 20 minute period. The resultant mixture was stirred at 75° C. for a further 10 minutes and then cooled to ambient temperature. The mixture was partitioned between diethyl ether and water. The organic phase was washed with water and with a saturated aqueous sodium chloride solution, dried ($MgSO_4$) and evaporated. The residue was purified by column chromatography on silica using a 21:4 mixture of petroleum ether (b.p. 40 to 60° C.) and ethyl acetate as eluent. There was thus obtained tert-butyl 3-[2-(2-methoxycarbonylethyl)-3,5-dimethyl-1,4-benzoquinonyl]-3-methylbutyrate (0.075 g); NMR Spectrum: ($CDCl_3$) 1.36 (s, 9H), 1.4 (s, 6H), 2.01 (s, 3H), 2.14 (s, 3H), 2.44 (t, 2H), 2.73 (t, 2H), 2.9 (s, 2H), 3.67 (s, 3H).

A mixture of the material so obtained, trifluoroacetic acid (2.5 ml), water (0.1 ml) and methylene chloride (2.5 ml) was stirred at ambient temperature for 2 hours. The mixture was evaporated and the residue was partitioned between diethyl ether and a dilute aqueous solution of sodium bicarbonate. The aqueous phase was acidified to pH2 by the aciton of dilute aqueous hydrochloric acid and extracted with diethyl ether. The organic phase was washed with a saturated aqueous solution of sodium chloride, dried ($MgSO_4$) and evaporated. There was thus obtained the required starting material (0.51 g); NMR Spectrurn: ($CDCl_3$) 1.36 (s, 6H), 1.93 (s, 3H), 2.07 (s, 3H), 2.32 (t, 2H), 2.67 (t, 2H), 2.95 (s, 2H) 3.61 (s, 3H).

EXAMPLE 21

Using an analogous procedure to that described in Example 1, 3-(5-allyl-2,3-dimethyl-1,4-benzoquinonyl)-3-ethylpentanoic acid was reacted with 4-[bis(2-chloroethyl)amino]phenol and the product was purified by column chromatography on silica using a 8.5:1.5 mixture of petroleumn ether (b.p. 40 to 60° C.) and ethyl acetate as eluent. The product so obtained was further purified by reversed-phase column chromatography on silica using an 80:20:1 mixture of methanol, water and acetic acid as eluent. There was thus obtained 4-[bis(2-chloroethyl)amino]phenyl 3-(5-allyl-2,3-dimethyl-1,4-benzoquinonyl)-3-ethylpentanoate in 79% yield; NMR Spectrum: ($CDCl_3$) 0.92 (t, 6H), 1.91 (s, 3H), 1.92 (s, 3H), 1.97 (m, 4H), 3.24 (s, 2H), 3.44 (m, 2H), 3.59 (t, 4H), 3.68 (t, 4H), 5.01 (m, 2H), 5.78 (m, 1H), 6.61 (d, 2H), 6.87 (d, 2H); Mass Spectrum: ($M+Na^+$) 542, 544 & 546.

The 3-(5-allyl-2,3-dimethyl-1,4-benzoquinonyl)-3-ethylpentanoic acid used as a starting material was obtained as follows:

A solution of a mixture of 2,3-dimethyl-1,4-benzoquinone (*J. Org. Chem.*, 1983, 48, 2932; 0.65 g) and ethyl 3-oxalooxy-3-ethylpentanoate (2.21 g) in methylene chloride (20 ml) was added to a stirred solution of sodium persulphate ($Na_2S_2O_8$; 2.27 g) in water (20 ml) and the mixture was stirred at ambient temperature for 10 minutes. Silver nitrate (0.081 g) was added and the mixture was stirred and heated to reflux for 2 hours. The mixture was cooled to ambient temperature and extracted with methylene chloride. The organic phase was washed with a saturated aqueous sodium chloride solution, dried ($MgSO_4$) and evaporated. The residue was purified by reversed-phase column chromatography on silica using an 80:20:1 mixture of methanol, water and acetic acid as eluent. There was thus obtained ethyl 3-(2,3-dimethyl-1,4-benzoquinonyl)-3-ethylpentanoate (0.146 g); NMR Spectrum: ($CDCl_3$) 0.78 (t, 6H), 1.15 (t, 3H), 1.62 (m, 2H), 1.82 (m, 2H), 1.88 (s, 2H), 2.0 (s, 3H), 2.01 (s, 3H), 4.0 (m, 2H), 6.44 (s, 1H).

After scaling up the previous reaction, a solution of sodium dithionite ($Na_2S_2O_4$: 15.2 g) in water (185 ml) was added to a solution of ethyl 3-(2,3-dimethyl-1,4-benzoquinonyl)-3-ethylpentanoate (10.2 g) in methanol (370 ml). Concentrated hydrochloric acid (10 ml) was then slowly added and the resultant mixture was stirred at ambient temperature for 90 minutes. The mixture was evaporated and the residue was extracted with diethyl ether, dried ($MgSO_4$) and evaporated. The residue was purified by column chromatography on silica using methylene chloride as eluent. There was thus obtained 4,4-diethyl-6-hydroxy-7,8-dimethyl-3,4-dihydrocoumarin (8.5 g); NMR Spectrum: ($CDCl_3$) 0.82 (t, 6H), 1.6 (m, 4H), 2.18 (s, 3H), 2.25 (s, 3H), 2.56 (s, 2H), 4.86 (s, 1H), 6.48 (s, 1H).

A mixture of a portion (4 g) of the material so obtained, allyl bromide (5.85 g), potassium carbonate (6.7 g) and DMF (50 ml) was stirred at ambient temperature for 90 minutes. The solvent was evaporated and the residue was partitioned between diethyl ether and dilute aqueous hydrochloric acid solution. The organic phase was washed with a saturated aqueous sodium chloride solution, dried ($MgSO_4$) and evaporated. The residue was purified by column chromatography on silica using a 4:1 mixture of petroleum ether (b.p. 40 to 60° C.) and ethyl acetate as eluent. There was thus obtained 6-allyloxy-4,4-diethyl-7,8-dimethyl-3,4-dihydrocoumarin (4.1 g); NMR Stectrum: ($CDCl_3$) 0.83 (t, 6H), 1.62 (m, 4H), 2.19 (s, 3H), 2.23 (s, 3H), 2.58 (s, 2H), 4.51 (m, 2H), 5.27 (d, 1H), 5.42 (d, 1H) 6.06 (m, 1H), 6.51 (s, 1H).

A mixture of the material so obtained and N,N-dimethylaniline (50 ml) was stirred and heated to 200° C. for 4.5 hours. The mixture was evaporated and the residue was purified by column chromatography on silica using a 9:1 mixture of petroleum ether (b.p. 40 to 60° C.) and ethyl acetate as eluent. There was thus obtained 5-allyl-4,4-diethyl-6-hydroxy-7,8-dimethyl-3,4-dihydrocoumarin (1.36 g); NMR Spectrum: ($CDCl_3$) 0.83 (t, 6H), 1.63 (m, 2H), 1.98 (m, 2H), 2.19 (s, 3H), 2.25 (s, 3H), 2.58 (s, 2H), 3.59 (m, 2H), 5.2 (d, 1H), 5.25 (d, 1H), 6.0 (m, 1H).

A solution of the material so obtained in acetonitrile (20 ml) was stirred and heated to reflux. A solution of ferric chloride hexahydrate (2.56 g) in a mixture of acetonitrile (25 ml) and water (25 ml) was added portionwise and the mixture was heated to reflux for 2 hours. The mixture was cooled to ambient temperature and the organic solvent was evaporated. The residue was extracted with diethyl ether. The organic extract was washed with a saturated aqueous sodium chloride solution, dried ($MgSO_4$) and evaporated. The residue was purified by column chromatography on silica using increasingly polar mixtures of petroleum ether (b.p. 40 to 60° C.) and ethyl acetate as eluent. There was thus obtained 3-(5-allyl-2,3-dimethyl- 1,4-benzoquinonyl)-3-ethylpentanoic acid (0.1 g); NMR Spectrum: ($CDCl_3$) 0.86 (t, 6H), 1.9 (m, 4H), 1.94 (s, 6H), 3.07 (s, 2H), 3.43 (m, 2H), 5.02 (m, 2H), 5.78 (m, 1H).

The ethyl 3-oxalooxy-3-ethylpentanoate used as a starting material was obtained as follows:

A solution of ethyl 3-ethyl-3-hydroxypentanoate (*J. Med. Chem.*, 1988, 31, 431; 7 g) in methylene chloride (32 ml) was added during 1 hour to a solution of oxalyl chloride (6.38 g) in methylene chloride (8 ml). The resultant mixture was stirred at ambient temperature for 2 days. The solvent was evaporated, the residue was dissolved in dioxane (20 ml) and added to cold water (150 ml). The mixture was stirred for 1 hour. The mixture was extracted with diethyl ether, dried ($MgSO_4$) and evaporated to give the required starting material as an oil (1 1.6 g); NMR Spectrum: ($CDCl_3$) 0.95 (t, 6H), 1.27 (t, 3H), 2.05 (m, 4H), 2.98 (s, 2H), 4.17 (m, 2H).

EXAMPLE 22

Using an analogous procedure to that described in Example 1, 3-(5-allyl-2,3-dimethyl-1,4-benzoquinonyl)-3,4-dimethylpentanoic acid was reacted with 4-[bis(2-chloroethyl)amino]phenol and the product was purified by column chromatography on silica using a 8.5:1.5 mixture of petroleum ether (b.p. 40 to 60° C.) and ethyl acetate as eluent. There was thus obtained 4-[bis(2-chloroethyl)amino] phenyl 3-(5-allyl-2,3-dimethyl-1,4-benzoquinonyl)-3,4-direthylpentanoate in 48% yield; NMR Spectrum: ($CDCl_3$) 0.96 (d, 3H), 0.98 (d, 3H), 1.5 (s, 3H), 1.9 (s, 3H), 1.92 (s, 3H), 2.45 (m, 1H), 2.55 (d, 1H), 3.37 (m, 1H), 3.57 (m, 5H), 3.67 (m, 4H), 3.77 (d, 1H), 4.96 (d, 1H), 5.02 (d, 1H), 5.7 (m, 1H), 6.62 (d, 2H), 6.84 (d, 2H); Mass Spectrum: (M+Na+) 542, 544 & 546.

The 3-(5-allyl-2,3-dimethyl-1,4-benzoquinonyl)-3,4-dimethylpentanoic acid used as a starting material was obtained as follows:

Using an analogous procedure to that described in the first paragraph of the portion of Example 21 which is concerned with the preparation of starting materials, 2,3-dimethyl-1,4-benzoquinone was reacted with methyl 3-oxalooxy-3,4-dimethylpentanoate to give methyl 3-(2,3-dimethyl-1,4-benzoquinonyl)-3,4-dimethylpentanoate in 36% yield; NMR Spectrum: ($CDCl_3$) 0.6 (d, 3H), 0.86 (d, 3H), 1.02 (s, 3H), 1.93 (s, 3H), 1.94 (s, 3H), 2.32 (, 1H), 2.45 (d, 1H), 3.31 (d, 1H), 3.45 (s, 3H), 6.38 (s, 1H).

The material so obtained was taken through the sequence of reactions disclosed in the further paragraphs of the portion of Example 21 which is concerned with the preparation of starting materials. There were thus obtained in turn: 6-hydroxy-4-isopropyl-4,7,8-trimethyl-3,4-dihydrocoumarin in 97% yield; NMR Spectrum: ($CDCl_3$) 0.81 (d, 3H), 0.91 (d, 3H), 1.22 (s, 3H), 1.81 (m, 1H), 2.17 (s, 3H), 2.23 (s, 3H), 2.41 (d, 1H), 2.81 (d, 1H), 4.7 (s, 1H), 6.54 (s, 1H); 6-allyloxy-4-isopropyl-4,7,8-trimethyl-3,4-dihydrocoumarin in 85% yield; NMR Spectrum: ($CDCl_3$) 0.81 (d, 3H), 0.91 (d, 3H), 1.24 (s, 3H), 1.82 (m, 1H), 2.18 (s, 3H), 2.23 (s, 3H), 2.43 (d, 1H), 2.79 (d, 1H), 4.52 (d, 2H), 5.28 (m, 1H), 5.41 (m, 1H), 6.08 (m, 2H), 6.56 (s, 1H); 5-allyl-6-hydroxy-4-isopropyl-4,7,8-trimethyl-3,4- dihydrocoumarin in 37% yield; NMR Spectrum: (CDCl₃) 0.88 (d, 3H), 0.96 (d, 3H), 1.42 (s, 3H), 2.03 (m, 1H), 2.19 (s, 3H), 2.23 (s, 3H), 2.4 (d, 1H), 2.72 (d, 1H), 3.41 (m, 1H), 3.75 (m, 1H), 4.98 (s, 1H), 5.13 (m, 1H), 5.26 (m, 1H), 6.05 (m, 1H); and 3-(5-allyl-2,3-dimethyl-1,4-benzoquinonyl)-3,4-dimethylpentanoic acid in 28% yield; NMR Spectrum: (CDCl₃) 0.9 (d, 3H), 0.92 (d, 3H), 1.93 (s, 3H), 1.95 (s, 3H), 2.32 (d, 1H), 2.39 (m, 1H), 3.32 (m, 1H), 3.52 (m, 1H), 3.6 (d, 1H), 4.94 (m, 1H), 5.0 (m, 1H), 5.8 (m, 1H).

The methyl 3-oxalooxy-3,4-dimethylpentanoate used as a starting material was obtained as follows:

A solution of methyl 3-hydroxy-3,4-dimethylpentanoate (*J. Amer. Chem. Soc.*, 1980, 102, 3614; 18.2 g) in methylene chloride (85 ml) was added during 1 hour to a solution of oxalyl chloride (18.05 g) in methylene chloride (18 ml). The resultant mixture was stirred at ambient temperature for 2 days. The solvent was evaporated, the residue was dissolved in acetone (50 ml) and added to cold water (450 ml). The mixture was stirred for 1 hour. The mixture was extracted with diethyl ether, dried (MgSO₄) and evaporated to give the required starting material (21.8 g); NMR Spectrum: (CDCl₃) 0.97 (d, 31H), 1.0 (d, 3H), 1.54 (s, 3H), 2.47 (m, 1H), 2.96 (d, 1H), 3.07 (d, 1H), 3.7 (s, 3H).

EXAMPLE 23

Using an analogous procedure to that described in Example 1, 2,3-dimethyl-3-(2,3,5-trimethyl-1,4-benzoquinonyl)butyric acid was reacted with 4-[bis(2-chloroethyl)amino]phenol and the product was purified by column chromatography on silica using a 8.5:1.5 mixture of petroleum ether (b.p. 40 to 60° C.) and ethyl acetate as eluent. There was thus obtained to give 4-[bis(2-chloroethyl)amino]phenyl 2,3-dimethyl-3-(2,3,5-trimethyl-1,4-benzoquinonyl)butyrate as an oil in 20% yield; NMR Spectrum: (CDCl₃) 1.25 (d, 3H), 1.45 (s, 3H), 1.50 (s, 3H), 1.95 (s, 3H), 1.97 (s, 3H), 2.21 (s, 3H), 3.60 (t, 4H), 3.67 (t, 4H), 3.85 (q, 1H), 6.61 (d, 2H), 6.82 (d, 2H); Mass Spectrum: (M+Na⁺) 502, 504 & 506.

The 2,3-dimethyl-3-(2,3,5-trimethyl-1,4-benzoquinonyl) butyric acid used as a starting material was obtained as follows:

Ethyl 2,3-dimethylbut-2-enoate (4.49 g) was added to a stirred mixture of 2,3,5-trimethylhydroquinone (4.58 g) and methanesulphonic acid (38 ml) which had been heated to 80° C. and the mixture was stirred at 80° C. for 2 hours. The mixture was poured onto a mixture of ice and water and the resultant mixture was extracted with ethyl acetate. The organic phase was washed with a saturated aqueous sodium chloride solution, dried (MgSO₄) and evaporated. The residue was purified by column chromatography on silica using a 4:1 mixture of petroleum ether (b.p. 40 to 60° C.) and ethyl acetate as eluent. There was thus obtained 6-hydroxy-3,4,4,5,7,8-hexamethyl-3,4-dihydrocoumarin (3.99 g); NMR Spectrum: (CDCl₃) 1.13 (d, 3H), 1.39 (s, 3H), 1.4 (s, 3H), 2.18 (s, 3H), 2.21 (s, 3H), 2.34 (s, 3H), 2.45 (m, 1H), 4.55 (s, 1H).

A solution of N-bromosuccinimide (1.3 g) in acetonitrile (39 ml) was added dropwise during 15 minutes to a stirred mixture of a portion (1.5 g) of the 3,4-dihydrocoumarin so obtained, water (12 ml) and acetonitrile (108 ml). The mixture was stirred at ambient temperature for 30 minutes. The resultant mixture was partitioned between diethyl ether and water. The organic phase was washed with a saturated aqueous sodium chloride solution, dried (MgSO₄) and evaporated. There was thus obtained the required starting material (1.7 g); NMR Spectrum: (CDCl₃) 1.15 (d, 3H), 1.35 (s, 3H), 1.42 (s, 3H), 1.99 (s, 6H), 2.16 (s, 3H), 3.67 (m, 1H).

EXAMPLE 24

Pharmaceutical Compositions

The following illustrate representative pharmaceutical dosage forms of the invention as defined herein (the active ingredient being teined "Compound X"), for therapeutic or prophylactic use in humans:

| | | |
|---|---|---|
| (a) | Tablet I | mg/tablet |
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium | 1.5 |
| (e) | Injection I | (50 mg/ml) |
| | Compound X | 5.0% w/v |
| | 1M Sodium hydroxide solution | 15.0% v/v |
| | 0.1M Hydrochloric acid | |
| | (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |
| (h) | Aerosol I | mg/ml |
| | Compound X | 10.0 |
| | Sorbitan trioleate | 13.5 |
| | Trichlorofluoromethane | 910.0 |
| | Dichlorodifluoromethane | 490.0 |
| (i) | Aerosol II | mg/ml |
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |
| (j) | Aerosol III | mg/ml |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |
| (k) | Aerosol IV | mg/ml |
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |
| (l) | Ointment | ml |
| | Compound X | 40 mg |
| | Ethanol | 300 μl |
| | Water | 300 μl |
| | 1-Dodecylazacycloheptan-2-one | 50 μl |
| | Propylene glycol | to 1 ml |

-continued

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan susquioleate, polysorbate 80, polyglycerol oleate or oleic acid.

what is claimed is:
1. An anti-tumour agent of the formula I

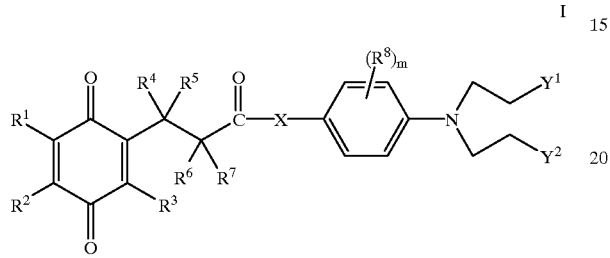

wherein $R^1$ is hydrogen, (1–4C)alkyl, (3–4C)alkenyl, (3–4C)alkynyl, hydroxy-(1–4C)alkyl, (1–4C)alkoxy-(1–4C)alkyl, amino-(1–4C)alkyl, (1–4C)alkylamino-(1–4C)alkyl, di-[(1–4C)alkyl]amino-(1–4C)alkyl, pyrrolidin-1-yl-(1–4C)alkl, piperidino-(1–4C)alkyl, morpholino-(1–4C)alkyl, piperazin-1-yl-(1–4C)alkyl, 1–4C)alkylpiperazin-1-yl-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino, (1–4C)alkylamino, (1–4C)alkenylamino, (3–4C)alkynylamino, di-[(3–4C)alkyl]amino, di-[(3–4C)alkenyl]amino, di-[(3–4C)alkynyl]amino, pyrrolidin-1-yl, piperidino, morpholino, piperazin-1-yl, 4-(1–4C)alkylpiperazin-1-yl, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, (2–4C)alkanoylamino, (2–4C)alkanoylamino-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbamoyl-(1–4C)alkylamino, N,N-di-[(1–4C)alkyl]carbamoyl-(1–4C)alkylamino, hydroxy, (1–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy or 4-(1–4C)alkylpiperazin-1-yl-(2–4C)alkoxy;

$R^2$ is hydrogen, (1–4C)alkyl, (3–4C)alkenyl, (3–4C)alkynyl, hydroxy-(1–4C)alkyl, (1–4C)alkoxy-(1–4C)alkyl, amino-(1–4C)alkyl, (1–4C)alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino, (1–4C)alkylamino, (3–4C)alkenylamino, (3–4C)alkynylamino, di-[(1–4C)alkyl]amino, di-[(3–4C)alkenyl]amino, di-[(3–4C)alkynyl]amino, pyrrolidin-1-yl, piperidino, morpholino, piperazin-1-yl, 4-(1–4C)alkylpiperazin-1-yl, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, (2–4C)alkanoylamino, (2–4C)alkanoylamino-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbamoyl-(1–4C)alkylamino, N,N-di-[(1–4C)alkyl]carbamoyl-(1–4C)alkylamino, hydroxy, (1–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy or 4(1–4C)alkylpiperazin-1-yl-(2–4C)alkoxy;

$R^3$ is hydrogen, (1–4C)alkyl, (3–4C)alkenyl, (3–4C)alkynyl, hydroxy-(1–4C)alkyl, (1–4C)alkoxy-(1–4C)alkyl, amino-(1–4C)alkyl, (1–4C)alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]carbamoyl-(1–4C)alkyl, amino, (1–4C)alkylamino, (3–4C)alkenylamino, (3–4C)alkynylamino, di-[(1–4C)alkyl]amino, di-[(3–4C)alkenyl]amino, di-[(3–4C)alkynyl]amino, pyrrolidin-1-yl, piperidino, morpholino, piperazin-1-yl, 4-(1–4C)alkylpiperazin-1-yl, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alklpiperazin-1-yl-(2–4C)alkylamino, (2–4C)alkanoylamino, (2–4C)alkanoylamino-(2–4C)alkylamino, carboxy-(1–4C)alkylamino, (1–4C)alkoxycarbonyl-(1–4C)alkylamino, carbamoyl-(1–4C)alkylamino, N-(1–4C)alkylcarbamoyl-(1–4C)alkylamino, N,N-di-[(1–4C)alkyl]carbamoyl-(1–4C)alkylamino, hydroxy, (1–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy or 4(1–4C)alkylpiperazin-1-yl-(2–4C)alkoxy;

$R^4$ is (1–4C)alkyl;
$R^5$ is (1–4C)alkyl;
$R^6$ is hydrogen or (1–4C)alkyl;
$R^7$ is hydrogen or (1–4C)alkyl;
X is oxygen;
m is 1 or 2 and each $R^8$ is independently hydrogen, halogeno, hydroxy, (1–4C)alkoxy, (2–4C)alkenyloxy, (2–4C)alkynyloxy, (1–4C)alkyl, (3–4C)alkenyl, (3–4C)alkynyl, amino, (1–4C)alkylamino, di-[(1–4C)

alkyl]amino, cyano, (2–4C)alkanoylamino, carboxy, (1–4C)alkoxycarbonyl, carbamoyl, N-(1–4C)alkylcarbamoyl or N,N-di-[(1–4C)alkyl-]carbamoyl;

$Y^1$ is halogeno, (1–4C)alkanesulphonyloxy, benzenesulphonyloxy or phenyl-(1–4C)alkanesulphonyloxy; and $Y^2$ is halogeno, (1–4C)alkanesulphonyloxy, benzenesulphonyloxy or phenyl-(1–4C)alkanesulphonyloxy;

and wherein any heterocyclic group in $R^1$, $R^2$ or $R^3$ is optionally substituted with 1, 2 or 3 (1–4C)alkyl substituents, and wherein any phenyl group in $Y^1$ or $Y^2$ when $Y^1$ and $Y^2$ is benzenesulphonyloxy or phenyl-(1–4C)alkanesulphonyloxy is optionally substituted with 1, 2 or 3 substituents selected from halogeno, nitro, cyano, trifluoromethyl, hydroxy, amino, (1–4C)alkyl, (1–4C)alkoxy, (1–4C)alkylamino and di-[(1–4C)alkyl]amino;

or a pharmaceutically-acceptable salt thereof; provided that at least one of $R^1$, $R^2$ and $R^3$ is other than hydrogen.

2. An anti-tumour agent of the formula I as claimed in claim 1 wherein each of $R^1$, $R^2$ and $R^3$ is independently hydrogen, methyl, ethyl, propyl, allyl, methylallyl, 2-hydroxyethyl, 3-hydroxypropyl, 2-methoxyethyl, 2-ethoxyethyl, 3-methoxy-propyl, 3-ethoxypropyl, 2-carboxyethyl, 3-carboxypropyl, 2-methoxycarbonylethyl, 2-ethoxy-carbonylethyl, 3-methoxycarbonylpropyl, 3-ethoxycarbonylpropyl, 2-(N-methylcarbamoyl)-ethyl, 3-(N-methylcarbamoyl)propyl, 2-(N,N-dimethylcarbamoyl)ethyl, 3-(N,N-dimethylcarbamoyl)propyl, methylamino, ethylamino, propylamino, isopropylamino, allylamino, 2-hydroxyethylamino, 3-hydroxypropylamino, 2-methoxyethylamino, 3-methoxypropylamino, 2-aminoethylamino, 3-aminopropylamino, 2-methylaminoethylamino, 3-methylaminopropylamino, 2-ethylaminoethylamino, 3-ethylaminopropylamino, 2-dimethylaminoethylamino, 2-diethylaminoethylamino, 3-dimethylaminopropylamino, 3-diethylaminopropylamino, 2-(pyrrolidin-1-yl)ethylamino, 3(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4-methylpiperazin-1-yl)ethylamino, 3-(4-methylpiperazin-1-yl)propylamino, 2-acetamidoethylamino, 2-propionamidoethylamino, 3-acetamidopropylamino, 3-propionamidopropylamino, 2-carboxyethylamino, 3-carboxypropylamino, 2-methoxycarbonylethylamino, 2-ethoxycarbonylethylamino, 2-(tert-butoxycarbonyl)ethylamino, 3-methoxycarbonylpropylamino, 3-ethoxycarbonylpropylamino, 3-(tert-butoxycarbonyl)propylamino, methoxy or ethoxy;

each of $R^4$ and $R^5$ is independently methyl, ethyl, propyl or isopropyl;

$R^6$ is hydrogen, methyl, ethyl, propyl or isopropyl;

$R^7$ is hydrogen or methyl;

X is oxygen;

m is 1 or 2 and each $R^8$ is independently hydrogen, fluoro, chloro, bromo, methoxy, ethoxy, methyl, ethyl, propyl, isopropyl or cyano; and each of $Y^1$ and $Y^2$ is independently chloro, bromo, iodo, methanesulphonyloxy, benzenesulphonyloxy or phenylmethanesulphonyloxy;

or a pharmaceutically-acceptable salt thereof; provided that at least one of $R^1$, $R^2$ and $R^3$ is other than hydrogen and provided that no more than two of $R^1$, $R^2$ and $R^3$ is a substituted amino group.

3. An anti-tumour agent of the formula I as claimed in claim 1 wherein $R^1$ is hydrogen, methyl, ethyl, propyl, allyl, methylallyl, 2-hydroxyethyl, 3-hydroxypropyl, 2-methoxyethyl, 3-methoxypropyl, 3-ethoxypropyl, 2-methoxycarbonylethyl, 2-ethoxycarbonylethyl, 3-methoxycarbonylpropyl, 3-ethoxycarbonylpropyl, 2-(N-methylcarbamoyl)ethyl, 3-(N-methylcarbamoyl)propyl, 2-(N,N-dimethylcarbamoyl)ethyl, 3-(N,N-dimethylcarbamoyl)propyl, methylamino, ethylamino, propylamino, isopropylamino, allylamino, 2-hydroxyethylamino, 3-hydroxypropylamino, 2-methoxyethylamino, 3-methoxypropylamino, 2-aminoethylamino, 3-aminopropylamino, 2-methylaminoethylamino, 3-methylaminopropylamino, 2-ethylaminoethylamino, 3-ethylaminopropylamino, 2-dimethylaminoethylamino, 2-diethylaminoethylamino, 3-dimethylaminopropylamino, 3-diethylaminoethylamino, 2-(pyrrolidin-1-yl)ethylamino, 3-(pyrrolidin-1-yl)propylamino, 2-piperidinoethylamino, 3-piperidinopropylamino, 2-morpholinoethylamino, 3-morpholinopropylamino, 2-(piperazin-1-yl)ethylamino, 3-(piperazin-1-yl)propylamino, 2-(4-methylpiperazin-1-yl)-ethylamino, 3-(4-methylpiperazin-1-yl)propylamino, 2-acetamidoethylamino, 2-propionamidoethylamino, 3-acetamidopropylamino, 3-propionamidopropylamino, 2-methoxycarbonylethylamino, 2-ethoxycarbonylethylamino, 2-(tert-butoxycarbonyl)ethylamino, 3-methoxycarbonylpropylamino, 3-ethoxycarbonylpropylamino, 3-(tert-butoxycarbonyl)propylamino, methoxy or ethoxy;

$R^2$ is hydrogen, methyl, ethyl, propyl, isopropyl, butyl, allyl, methylallyl, methoxy or ethoxy;

$R^3$ is hydrogen, methyl, ethyl, propyl, isopropyl, butyl, allyl, methyallyl, methoxy or ethoxy;

$R^4$ is methyl, ethyl, propyl or isopropyl;

$R^5$ is methyl, ethyl, propyl or isopropyl;

$R^6$ is hydrogen, methyl, ethyl, propyl or isopropyl;

$R^7$ is hydrogen or methyl;

X is oxygen;

m is 1 or 2 and each $R^8$ is independently hydrogen, fluoro, chloro, bromo, methoxy, ethoxy, methyl, ethyl, propyl or isopropyl;

$Y^1$ is chloro, bromo, iodo or methanesulphonyloxy; and $Y^2$ is chloro, bromo, iodo or methanesulphonyloxy;

or a pharmaceutically-acceptable salt thereof; provided that at least one of $R^1$, $R^2$ and $R^3$ is other than hydrogen.

4. An anti-tumour agent of the formula I as claimed in claim 1 wherein $R^1$ is hydrogen, methyl, ethyl, propyl, allyl, 2-methoxyethyl, methylamino, ethylamino, propylamino, isopropylamino, allylamino, 2-dimethylaminoethylamino, 2-diethylaminoethylamino; 2-(pyrrolidin-1-yl)ethylamino, 2-piperidinoethylamino, 2-morpholinoethylamino, 2-(piperazin-1-yl)ethylamino, 2-(4-methylpiperazin-1-yl)ethylamino, 2-acetamidoethylamino, methoxy or ethoxy;

$R^2$ is hydrogen, methyl, ethyl, propyl, allyl, methoxy or ethoxy;

$R^3$ is hydrogen, methyl, ethyl, propyl, isopropyl, allyl, methoxy or ethoxy;

$R^4$ is methyl or ethyl;

$R^5$ is methyl or ethyl;

$R^6$ is hydrogen, methyl or ethyl;

$R^7$ is hydrogen;

X is oxygen;

m is 1, $R^8$ is located meta to X and $R^8$ is hydrogen, fluoro, chloro, methyl, ethyl, propyl or isopropyl; and each of $Y^1$ and $Y^2$ is chloro, bromo or iodo;

or a pharmaceutically-acceptable salt thereof; provided that at least one of $R^1$, $R^2$ and $R^3$ is other than hydrogen.

5. An anti-tumour agent of the formula I as claimed in claim 1 wherein $R^1$ is hydrogen, methyl, 2-methoxyethyl, isopropylamino, 2-morpholinoethylamino, 2-acetamidoethylamino or methoxy;

$R^2$ is hydrogen, methyl, allyl or methoxy;

$R^3$ is methyl, ethyl, propyl or allyl;

each of $R^4$ and $R^5$ is methyl;

$R^6$ is hydrogen or methyl;

$R^7$ is hydrogen;

X is oxygen;

m is 1 and $R^8$ is hydrogen; and each of $Y^1$ and $Y^2$ is chloro;

or a pharmaceutically-acceptable salt thereof.

6. An anti-tumour agent of the formula I as claimed in claim 1 selected from:

4-[bis(2-chloroethyl)amino]phenyl 3-[2-(2-acetamidoethylamino)-3-methoxy-5-methyl-1,4-benzoquinonyl]-3-methylbutyrate, 4-[bis(2-chloroethyl)amino]phenyl 3-[2-(2-methoxyethyl)-3,5-dimethyl-1,4-benzoquinonyl]-3-methylbutyrate, 4-[bis(2-chloroethyl)amino]phenyl 3-[3-allyl-2,5-dimethyl-1,4-benzoquinonyl]-3-methylbutyrate, 4-[bis(2-chloroethyl)amino]phenyl 3-methyl-3-(2,3,5-trimethyl-1,4-benzoquinonyl)butyrate, 4-[bis(2-chloroethyl)amino]phenyl 3-(2,5-dimethyl-1,4-benzoquinonyl)-3-methylbutyrate, 4-[bis(2-chloroethyl)amino]phenyl 3-[3-methoxy-5-methyl-2-(2-morpholinoethylamino)-1,4-benzoquinonyl]-3-methylbutyrate and 4-[bis(2-chloroethyl)amino]phenyl 2,3-dimethyl-3-(2,3,5-trimethyl-1,4-benzoquinonyl)butyrate;

or a pharmaceutically-acceptable salt thereof.

7. An anti-tumour agent of the formula I, or a pharmaceutically-acceptable salt thereof, as claimed in any of claims 1 to 6 wherein the reduction potential of said anti-tumour agent of the formula I, or a pharmaceutically-acceptable salt thereof is in the range −200 to −475 mV.

8. A process for the preparation of an anti-tumour agent of the formula I, or a pharmaceutically-acceptable salt thereof, as claimed in claim 1 which comprises: the reaction of an acid of the formula II

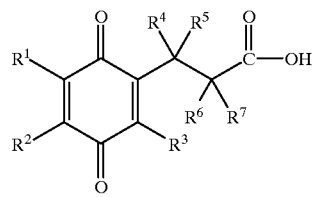

wherein each of $R^1$, $R^2$, $R^3$, $R^4$, $R^5$, $R^6$ and $R^7$ has any of the meanings defined in claim 1, or a reactive derivative thereof, with a compound of the formula III

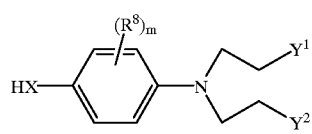

wherein each of X, $R^8$, m, $Y^1$ and $Y^2$ has any of the meanings defined in claim 1; and when a pharmaceutically-acceptable salt of a compound of the formula I is required, it may be obtained by reaction of said compound with a suitable acid or base using a conventional procedure and when an optically active form of a compound of the formula I is required, it may be obtained by carrying out the aforesaid process using an optically active starting material, or by resolution of a racemic form of said compound using a conventional procedure.

9. A pharmaceutical composition which comprises an anti-tumour agent of the formula I, or a pharmaceutically-acceptable salt thereof, as claimed in claim 1 in association with a pharmaceutically- acceptable diluent or carrier.

10. A method of treating a warm-blooded animal having a tumour, which method comprises administering to said animal an effective amount of the anti-tumour agent of formula I, or a pharmaceutically-acceptable salt thereof, as claimed in claim 1.

11. A method for producing an anti-proliferative effect in a warm-blooded animal in need thereof, which method comprises administering to said animal an effective amount of the anti-tumour agent of formula I, or a pharmaceutically-acceptable salt thereof, as claimed in claim 1.

* * * * *